United States Patent [19]
Saunders et al.

[11] Patent Number: 5,674,699
[45] Date of Patent: Oct. 7, 1997

[54] TWO-PHASE OPTICAL ASSAY

[75] Inventors: Alexander Saunders; Michael Allan Zarowitz, both of San Carlos, Calif.

[73] Assignee: Chronomed, Inc., San Carlos, Calif.

[21] Appl. No.: 361,832

[22] Filed: Dec. 22, 1994

Related U.S. Application Data

[63] Continuation-in-part of Ser. No. 73,450, Jun. 8, 1993, abandoned.

[51] Int. Cl.$^6$ .................. G01N 33/543; G01N 33/548; G01N 33/573; G01N 33/72
[52] U.S. Cl. .................. 435/7.93; 435/7.1; 435/7.4; 435/7.8; 436/518; 436/528; 436/529; 436/67; 436/172
[58] Field of Search .................. 435/7.4, 7.8, 7.93, 435/7.94, 7.1; 436/67, 501, 518, 528, 529, 531, 532, 533, 534, 172, 805

[56] References Cited

U.S. PATENT DOCUMENTS

| | | | |
|---|---|---|---|
| 3,647,300 | 3/1972 | Skala | 356/73 |
| 3,862,303 | 1/1975 | Anderson | 436/531 |
| 4,016,043 | 4/1977 | Schuurs et al. | 435/7.94 |
| 4,034,074 | 7/1977 | Miles | 436/518 |
| 4,067,959 | 1/1978 | Bolz | 435/7.92 |
| 4,115,535 | 9/1978 | Glaever | 436/526 |
| 4,144,452 | 3/1979 | Harte | 250/302 |
| 4,159,896 | 7/1979 | Levine et al. | 436/177 |
| 4,185,084 | 1/1980 | Mochida et al. | 435/7.93 |
| 4,197,361 | 4/1980 | Hoff et al. | 435/5 |
| 4,255,385 | 3/1981 | Stroupe et al. | 436/67 |
| 4,258,001 | 3/1981 | Pierce et al. | 422/56 |
| 4,260,516 | 4/1981 | Moore | 436/15 |
| 4,269,605 | 5/1981 | Dean et al. | 436/67 |
| 4,279,617 | 7/1981 | Masson et al. | 436/509 |
| 4,283,382 | 8/1981 | Frank et al. | 436/533 |
| 4,292,296 | 9/1981 | Parsons, Jr. | 436/518 |
| 4,350,760 | 9/1982 | Nicolas et al. | 435/7.92 |
| 4,376,110 | 3/1983 | David et al. | 435/7.94 |
| 4,407,961 | 10/1983 | Sanders | 436/67 |
| 4,409,335 | 10/1983 | Hanamoto et al. | 436/67 |
| 4,459,358 | 7/1984 | Berke | 436/170 |
| 4,504,584 | 3/1985 | Kitaura et al. | 435/253.5 |
| 4,567,754 | 2/1986 | Wardlaw et al. | 422/55 |
| 4,629,692 | 12/1986 | Dean | 436/67 |

(List continued on next page.)

OTHER PUBLICATIONS

Harlow et al, 1988. *Antibodies. A Laboratory Manual*, Cold Spring Harbor Laboratory, Cold Spring Harbor. pp. 528–530, 570–573, 602–603, 605, and 610.

Borun, E. Raymond, et al, "The Distribution of FE$^{59}$ Tagged Human Erythrocytes In Centrifuged Specimens as a Function of Cell Age", *J. Clinical Investigation*, 36:676 (1957).

Deeg, Rolf et al, "A New Approach to Photometry of Glycated Hemoglobin in Human Blood", *Clinical Chemistry*, vol. 30, No. 5, pp. 790–793, 1984.

Fluckiger, R. et al, "In Vitro Synthesis of Hemoglobin $A_{Ic}$", *Febs Letters*, vol. 71, No. 2, pp. 356–361, Dec. 1976.

Fluckiger, R. et al, "Quantitation of Glycosylated Hemoglobin by Boronate Affinity Chromatography", *Diabetes*, vol. 33, pp. 73–76, 1984.

(List continued on next page.)

*Primary Examiner*—Paula K. Hutzell
*Assistant Examiner*—James L. Grun
*Attorney, Agent, or Firm*—Iver P. Cooper

[57] ABSTRACT

A method is provided for measuring an analyte in a sample comprising adding substantially transparent particles to a sample in solution or suspension, said particles having an affinity for said analyte; fractionating the particles from the solution or suspension to form a particle-rich fraction and a substantially particle-free fraction; optically reading the particle-rich fraction at a first and a second wavelength; optically reading the substantially particle-free fraction at at least the first wavelength; and correlating the readings through the particle-rich fraction and the substantially particle-free fraction of the sample, with similar measurements in a particle-containing "blank" to obtain a quantitative determination of the analyte originally present in the sample.

18 Claims, 9 Drawing Sheets

U.S. PATENT DOCUMENTS

| | | | |
|---|---|---|---|
| 4,670,381 | 6/1987 | Frickey et al. | 435/7.93 |
| 4,672,038 | 6/1987 | Jaekel et al. | 435/5 |
| 4,762,798 | 8/1988 | Deutsch | 436/67 |
| 4,774,965 | 10/1988 | Rodriguez et al. | 128/771 |
| 4,775,637 | 10/1988 | Sutherland et al. | 436/527 |
| 4,778,752 | 10/1988 | Curtiss | 435/7.92 |
| 4,806,468 | 2/1989 | Wagner et al. | 436/67 |
| 4,818,710 | 4/1989 | Sutherland et al. | 436/527 |
| 4,847,209 | 7/1989 | Lewis et al. | 436/533 |
| 4,861,728 | 8/1989 | Wagner | 436/67 |
| 4,876,188 | 10/1989 | Smith et al. | 435/7.92 |
| 4,981,362 | 1/1991 | DeJong et al. | 356/436 |
| 5,006,459 | 4/1991 | Kung et al. | 435/7.23 |
| 5,074,658 | 12/1991 | Tavlarides et al. | 356/73 |
| 5,093,221 | 3/1992 | Chen et al. | 430/257 |
| 5,110,745 | 5/1992 | Kricka et al. | 436/87 |
| 5,252,492 | 10/1993 | Yoshikami | 436/501 |

OTHER PUBLICATIONS

Kamentsky, Louis A., et al, "Spectrophotometer: New Instrument for Ultrarapid Cell Analysis", Science, vol. 15, pp. 630–631, Oct. 1965.

Klenk, Dennis C. et al, "Determination of Glycosylated Hemoglobin by Affinity Chromatography: Comparison with Colorimetric and Ion–Exchange Methods, and Effects of Common Interferences", Clinical Chemistry, vol. 28, No. 10, pp. 2088–2094, 1982.

Ornstein, Leonard, "The Distributional Error in Microspectrophotometry", Laboratory Investigation, vol. 1, No. 2, pp. 250–265, 1952.

Patau, Klaus, "Absorption Microphotometry of Irregular–Shaped Objects", Chromosoma, vol. 5, pp. 341–362, 1952.

Pecararo, Roger E. et al, "Comparison of a Colorimetric Assay for Glycosylated Hemoglobin with Ion–Exchange Chromatography", Diabetes, vol. 28, pp. 1120–1125, 1979.

Saunders, Alex M., "Retrospective Time–Resolved Testing: Model I—Time–Resolved Glycohemoglobin", Clinical Chemistry, vol. 37, No. 9, pp. 1531–1533, 1991.

Tietz, 1986. *Textbook of Clinical Chemistry*. W.B. Saunders Co., Philadelphia. pp. 65–66, 1532–1533.

Clausen, 1986. *Immunochemical Techniques for the Identification and Estimation of Macromolecules*. Elsevier/North–Holland Biomedical Press, Amsterdam. pp. 277–278.

TWO-PHASE OPTICAL ASSAY

This application is a continuation-in-part of Ser. No. 08/073,450, filed Jun. 8, 1993, now abandoned hereby incorporated by reference its entirety.

BACKGROUND OF THE INVENTION

1. Field of the Invention

The present invention relates to a method and apparatus for quantifying analytes in a sample. It is particularly useful for measuring glycosylated and unglycosylated hemoglobin in a blood sample.

2. Description of the Background Art

Hemoglobin is made up of four polypeptide chains, each of which bears a heme group. Over 90% of normal human adult hemoglobin, HbA, is made up of two alpha globin and two beta globin chains.

While hemoglobin HbA0 is unglycated, several glycated species are known. Based on the order of their elution from a cation-exchange resin, these are called HbA1a1, HbA1a2, HbA1b and HbA1c. They are formed by the nonenzymatic attachment of fructose-1,6-diphosphate, glucose-6-phosphate, an unidentified carbohydrate, or glucose, respectively, to the beta chain of the hemoglobin. Hemoglobin can also be glycated on the alpha chain, but these species are not readily separable from unglycated hemoglobin on the basis of charge.

HbA1c is formed by a two step process. First, the glucose reacts with an amino group of the hemoglobin (either the N-terminal or the epsilon amino group of a lysine) to from an aldimine (Schiff base), also known as pre-A1c or "labile" A1c. Then the pre-A1c undergoes an Amadori rearrangement to yield a ketoeunine, the mature or "stable" A1c.

Measurement of glycated hemoglobin is a clinically accepted means of assessing glycemic control in diabetics. GHb values reflect blood glucose levels over the circulatory life of the erythrocyte (about 120 days). In uncontrolled or poorly controlled diabetics, glycated hemoglobin values may be two or three times as high as in non-diabetics, while meticulously controlled diabetics may have GHb levels near or in the normal range.

The principal plasmaproteins (albumin and the globulins) also appear in glycated form, however, the glycated plasma proteins (GPP) cannot be separated from their non-glycated progenitors on the basis of charge. GPP values reflect blood glucose levels over the circulatory life of the plasma proteins (for albumin, about three weeks). In view of the shorter half life of GPPs relative to GHb, GPP responds more quickly than does GHb to loss of glycemic control. GPP measurement may be particularly useful in patients whose pregnancies are complicated by diabetes.

Affinity Assay Methods

Many analytes of interest have one or more characteristic wavelengths of absorbance or fluorescence. In theory, the amount of such an analyte in the sample may be determined by performing a suitable optical measurement on the sample. In practice, the accuracy of this simple analysis is impaired if any of the other components of the sample also absorb or fluoresce at that wavelength. Therefore, it is customary to use a solid phase affinity reagent to separate the analyte from interfering substances.

Chromatographic Effluent Assays. In conventional solid-liquid mini-chromatography assay, an affinity reagent is attached to a solid phase (e.g., beads in a column), and the sample is introduced into a liquid phase which is passed over the solid phase. Components which are strongly bound by the affinity reagent will be substantially retarded in the passage, weakly bound constituents will move more quickly through the liquid phase, and components which do not interact at all with the affinity reagent will move fastest of all. The constituents of the sample can therefore be separated, with the least bound constituent collected in the earlier effluent fractions and the strongly bound constituents appearing later. The presence of an analyte of interest in the sample is then detected by placing a detector in the flow path between the column and the effluent collector, or by collecting the fractions in separate vessels, and measuring the amount of analyte in each vessel.

Of course, a given analyte will not flow out all at once. There will be trace amounts of analyte in one fraction, a more substantial amount in another fraction, the analyte will peak in a third amount, and then will taper off in later fractions. If the constituent is to be quantified, then it is necessary to measure the amount (e.g., by absorbance) of analyte in each fraction as it exits the column, and then integrate the values over time.

When the solid phase takes the form of particles, the particles used are usually very small (so the capture area is great, and analyte is rapidly removed from the moving phase). Because of the size of the particles, it is difficult to measure optically even a colored or fluorescent analyte in site, as there is considerable light loss due to light scattering by the particles. In general, while the presence of analyte in a retained fraction on a minicolumn may be visible, it is not possible to measure the analyte while it is thus still bound to derivatized particles in the minicolumn.

A chromatographic mini-column may be used to measure GHbs, GPPs and other analytes if a suitable affinity reagent is available. In the case of GHbs and GPPs, a boronate may be used as the affinity reagent. The boronate will complex with the diol groups of the glycated analyte. Other sugar-specific binding agents, such as lectins and certain antibodies, are also known in the art. A number of workers have used a chromatographic column to separate glycosylated hemoglobin from non-glycosylated hemoglobin by means of an affinity reagent specific to the glycosylated form bound to the solid phase: Dean et al., U.S. Pat. No. 4,269,605; Klen et al., *Clinical Chemistry*, 28(1): 2088–2094 (1982); Kricka et al., *Clinical Chemistry* 37(9): 1991 (1991); Pecoraro et al, *Diabetes,* 28: 1120 (1979); Fluckiger et al., *Diabetes* 33: 73–76 (1984) and Saunders, *Clinical Chemistry* 37: 1531 (1991). See also Sanders, in U.S. Pat. No. 4,407,961, who separates glycoslyated hemoglobin from non-glycosylated hemoglobin using a column which adsorbs the non-glycosylated form. The light absorbance of the eluate and of whole blood lysate are compared.

While mini-columns have been used to measure glycohemoglobin and other analytes, they present several disadvantages. To accomplish the assay, one must wash the sample into the column, stop the flow, and then repeatedly measure out an exact volume of eluent to the top of the column and collect effluent at the bottom. A container is needed for each effluent fraction, and fraction after fraction must be placed in a spectrophotometer and compared to a blank. Finally, the amounts of analyte in the fractions must be added up. There are thus numerous manipulations involved.

Nor is that the only disadvantage of the mini-column approach. Large volumes of both eluting agent and particles are needed.

In the example given above, the process of analyzing the sample is continuous. However, batch processes are also possible. In this case, there is no need for the liquid phase to flow at all. Rather, the sample is introduced into the liquid phase, which is contacted with the solid phase. After a suitable incubation period, the two phases are separated (e.g., by decanting the liquid and washing off the solid). An eluting agent is then added to the solid phase, and the amount of analyte eluted is measured. See, Clausen, *Immunochemical Technology for the Identification and Estimation of Macromolecules*, pp. 277–278 (2d ed. 1981).

While the batch method ameliorates the complexity of the analyte collection and analysis, repeated elution is still required to assure complete recovery of the analyte, and the method still requires large volumes of eluting agent and beads.

Agglutination Assays. In an agglutination assay, an affinity reagent is coupled to agglutinable particles. This reagent is then mixed with the sample solution. If the analyte is polyvalent, then two or more particles can conjugate simultaneously to a signal molecule of analyte, and each of these particles can in turn conjugate to other molecules of analyte. This networking of particles and analyte results in the formation of an agglutinate, and thus in increased turbidity. The degree of agglutination is expected to be directly proportional to the amount of the analyte in the sample. The particles used in an agglutination assay must be nonporous because agglutination is a surface reaction, and penetration of the analyte to the inside of the particles would reduce analyte availability on the surface.

If the analyte is monovalent, a secondary reagent, a polyvalent analyte analogue, is used. This analogue competes with the actual analyte for the bindable particles, and, because it is multivalent, can form an agglutinate. The degree of agglutination is expected to be inversely proportional to the amount of analyte in the sample because of the competitive nature of the reactions.

Lewis et al. in U.S. Pat. No. 4,847,209, disclose an agglutination assay for determination of HbA1c. An antibody which specifically binds HbA1c is attached to latex particles (0.04–1.2 microns). Also, an agglutinator reagent, presenting a plurality of glycated peptide binding sites for the antibody, is prepared. These reagents are incubated with the blood sample. Since, according to Lewis, hemoglobin can nonspecifically agglutinate such particles at normal pH, the pH is brought above 8.5. Twenty minutes after the reagents are dispensed, the mixture is examined photometrically for increased turbidity attributable to agglutination. Lewis emphasizes that a latex blank must be included in each run.

Frank et al., in U.S. Pat. No. 4,283,382, disclose a fluorescent immunoassay using latex beads (0.01–0.2 microns, i.e., a "colloidal dispersion") which are labelled with the fluorophore (a rare earth chelate) and also coupled or coated with an analyte binding reagent such as an antigen or antibody. If the sample contains the corresponding polyvalent analyte, the latex beads are agglutinated, and the agglutinate settles to the bottom. The fluorescence of the supernatant is then compared with that of the settled bead volume.

Giaver, in U.S. Pat. No. 4,115,535, discloses the use of two different types of particles in a qualitative binding assay. Both particles bear an analyte-binding agent such as an antibody. The first type facilitates separation, and my be magnetic or high density particles. The second type provides detectability, such as fluorescent or colored particles. Theoretically the analyte causes agglutination of both types of particles, so that the first type will draw the second type along. While the inventor alludes to a density-based separation, the separations disclosed are generally electromagnetic.

Other Hererogenous Affinity Binding Assays. A "heterogeneous" affinity binding assay is one in which the components of a sample may either remain in the liquid phase or become bound to a solid phase, and an affinity reagent is used to concentrate the analyte into one of the phases. While the chromatographic and agglutination assays discussed above are conducted in heterogeneous systems, they require either that the analyte be eluted, or that the solid phase participate actively in signal production. We now review a third class of heterogeneous affinity binding assays, which do not have these requirements. These assays may be conducted in either a "sandwich" (direct) or a "competitive" (indirect) format.

In a competitive assay, analyte in the sample is allowed to compete with a labeled analyte analogue for the ligand binding sites of the solid phase reagent. Unbound sample and analogue are washed off the solid phase, and the signal produced by the bound analyte analogue should be inversely proportional to the level of analyte in the sample. In a variation on this assay, the analyte analogue is coupled to the solid phase and the affinity reagent is labeled.

Curriss, U.S. Pat. No. 4,778,752, used a competitive assay to determine glycated plasma proteins. The affinity reagent was a murine monoclonal antibody specific for glucitolysine and was labeled with a radioactive goat anti-murine Ig. The solid phase analyte analogue was a microtiter plate coated with glc(RED)-LDL, produced by first reducing and then glucosylating LDL.

The approach of Kricka, U.S. Pat. No. 5,110,745 is similar; Kricka's preferred affinity reagent is a boronate compound, his preferred analyte analogue is glycated BSA, and his preferred label is a chromogen, NBT. The solid phase was a flat membrane.

In a "sandwich" assay, a first affinity reagent is immobilized on a solid phase, such as a microtiter plate, a test tube wall, or a dipstick, and a second affinity reagent is labeled, e.g., with a radioisotope, an enzyme, or a fluorophore. The sample is incubated both with the solid phase reagent, which captures the analyte, and with the labeled reagent, which also binds the analyte, forming a ternary complex (the "sandwich"). (The two incubations may be performed either simultaneously, or in either order.) The solid and liquid phases are separated, to remove unbound labeled reagent, and the quantity of label remaining on the solid phase is determined. The signal is directly proportional to the amount of analyte since the label is bound to the analyte.

The labeling reagent may be dispensed with if the analyte is intrinsically detectable. It is then no longer strictly proper to call the assay a "sandwich" assay, as no ternary complex is formed, but the assay is still one in which analyte is measured directly.

Sutherland et al., in U.S. Pat. Nos. 4,775,637 and 4,818,710, disclose a system for measuring glycosylated hemoglobin in a solution also containing non-glycosylated hemoglobin. In this system, there are two waveguides, one bearing antibodies to glycosylated hemoglobin, the other being blocked to prevent nonspecific binding of Hb. Light is directed into the waveguide cell at an angle, and, in the absence of analyte, the beam is repeatedly reflected back and forth off the walls of the waveguide, thereby traversing it. As glycosylated Hb builds up on the antibody-coated wall, light loss increases.

Deutsche, in U.S. Pat. No. 4,762,798, discloses a method for measuring total hemoglobin and glycohemoglobin by (1) measuring total optical absorbance at a total hemoglobin-specific wavelength, (2) adding an adsorbent for unglycosylated hemoglobin, (3) decanting the unbound glycosylated hemoglobin, and (4) measuring the latter by optical absorbance. In this process, the hemoglobins must be separated from each other for measurement, and time must elapse between the measurements to remove hemoglobin. This assay thus requires time between measurements to remove unglycated hemoglobin, making the time required for each assay unduly long.

Wagner, in U.S. Pat. No. 4,861,728, discloses an assay for glycosylated hemoglobin and non-glycosylated hemoglobin simultaneously in the same vessel. One reagent is a solid phase reagent which binds both $HbA_0$ and HbA1c. The solid phase is preferably a dipstick. The reagent is reacted with the sample, and the unbound components of the sample are washed off. The color of the solid phase is then read.

Next, the bound hemoglobins are incubated with a second reagent which reacts only with the glycoside portion of HbA1c, and is conjugated with a fluorescent dye. The unbound second reagent is removed, and the dye absorption of incident light indicates the level of HbA1c.

The Wagner method is a hybrid of an assay for total hemoglobin and an assay for HbA1c. The first assay requires that unbound components of the sample be washed off. Thus, buffer is consumed. Moreover, some of the analyte may leach out. In the second stage, an expensive second reagent is required to selectively label the HbA1c. More buffer is needed to wash off the unbound second reagent, and more analyte can be lost in the process.

While it is theoretically possible to use a particulate solid phase, such as that commonly used in agglutination assays, in an assay like Wagner's, it would not be considered a rational approach, as the particles would complicate the analysis. In order for the solid and liquid phases to be optically distinguished, they would have to be physically separated, e.g., by settling or centrifugation. However, the particle size of the particles used in agglutination assays is chosen so that the particles will not settle out unless they are agglutinated. Indeed, with the particle sizes preferred in the art, it would take a high speed centrifuge to achieve sedimentation, absent agglutination.

Once the particles are sedimented, their very small size results in extensive surface and internal light scattering, with consequent light loss. The optical effect of the analyte, or of the label, may be small in comparison, making it difficult to accurately quantify the amount of analyte present.

An additional problem is that potentially optically interfering constituents of the sample will remain in the particulate solid phase, in the "free volume" (the interstices between the particles and the pores of the particles), although unbound by the affinity reagent. For this reason, the art would have expected to need to wash the particles extensively to remove these interfering components, which in turn would require consumption of large quantities of buffer and, incidentally, could leach out some of the bound analyte. Dipsticks and test tubes are less able to retain unbound constituents to begin with, and are easier to wash as well. The art therefore teaches strongly against the use of a particulate solid phase reagent other than in a conventional agglutination assay.

Homogeneous Affinity Binding Assays. Homogeneous assays are performed in a single phase, as bound and unbound constituents are distinguished without the need for phase separation, as a consequence of the effect of the complex on the signal produced by the system.

Wagner et al., in U.S. Pat. No. 4,806,468, disclose measuring hemoglobin and glycosylated hemoglobin in the same container by their absorbance at different wavelengths. This assay depends on the finding that the peroxidase activity of hemoglobin is blocked by anti-Hb, while the peroxidase activity of HbA1c is retained when it binds to anti-HbA1c. Moreover, anti-bA1c inhibits the binding of anti-Hb to HbA1c. In the assay, the red blood cells are lysed to release the Hb, and a mixture of anti-Hb and anti-HbA1c is added. The total Hb ($A_0$ and A1c) is measured by determining the absorbance at 416 nm or 540 nm. A peroxidase substrate is added, and the absorbance of the peroxidase product is detected at a different wavelength, e.g., 620 nm. While two different wavelengths are used, there is no sequestration of glycohemoglobin in one portion of the vessel, or separate imaging of different zones of the vessel. The antibodies are provided in solution form rather than in the solid phase. Similarly, Deeg et al., in *Clinical Chemistry* 30(5): 790–793 (1984) disclose the measurement of glycated hemoglobin by adding a reactant which blocks normal hemoglobin from binding to haptoglobin but not glycated hemoglobin.

Dean, U.S. Pat. No. 4,629,692 describes use of an antibody which recognizes Amadori-rearranged glucose in immunoassays for nonenzymatically glycosylated proteins in biological fluids. While he refers in passing to "agglutination techniques", his preference is for a homogeneous enzyme substrate-labeled fluorescent immunoassay employing beta-galactosylumbelliferone labels conjugated to an analyte analogue. The enzyme beta-galactosidase will normally cleave off the beta-galactosyl group to release a highly fluorescent umbelliferone derivative, however, if the conjugate is bound by Dean's antibody, cleavage is inhibited and fluorescence generation is reduced.

Miscellaneous Assays. Anderson, in U.S. Pat. No. 3,862,303, discloses a binding assay in which the analyte being measured binds to latex beads which have a specific affinity binding agent attached. The binding analyte is detected by its alteration of the effective density of the bead. After incubation with sample, the beads are centrifuged in a liquid having a density gradient. The beads gravitate to the appropriate layer, depending on the amount of analyte bound. The binding may be observed without separating bound from free analyte. This method places stringent requirements on the size and density of the beads, and it is the opacity of the beads, not the specific absorbance of the analyte, that provides the assay results. Making the beads transparent would defeat the assay. The beads are distributed throughout the density gradient column.

Optical Measurements, Generally

Tietz, ed., Textbook of Clinical Chemistry, page 66 (W. B. Saunders Co., 1986) teaches that "background interference can often be eliminated or minimized either by inclusion of blanks or by reading absorbance at two or three wavelengths". However, he does not address the complexities of light scattering by particles, in particular, the effect of analyte absorption on light scattering by the particles. Use of blanks, which do not, by definition, include analyte, cannot correct for such effects. Nor does Tietz discuss whether this effect is wavelength dependent; reading absorbance at multiple wavelengths would not be expected to correct for an effect which could be wavelength dependent to an unpredictable degree.

Kamensky, et al., Science, 15:630 (1965) observed human cells passing through a flow cytometer by measuring their absorption at 2537 Å and their scattering at 4100 Å. The former parameter was used to estimate nucleic acid content, and the latter to derive the cell size or mass.

Patau, Chromosoma, 5:341–362 (1952) discusses the problems associated with absorption microphotometry of irregularly shaped objects. One error is caused by the non-uniformity of the dye distribution in the object. Patau suggests correcting for this error by measuring absorption at two different wavelengths, with one preferably being twice the other. The measurements must be made both with and without the object. Another error is caused by the stray light entering the photo-receiver without passing through the object. Patau emphasizes that the larger, less transparent the object the larger the errors. Ornstein, Lab. Invest., 1:250–265 (1952) discusses the mathematics of the distributional error, and provided inspiration to Patau.

SUMMARY OF THE INVENTION

The present invention is directed to an assay which overcomes the deficiencies of the prior art by optical measurement of the quantity of otherwise soluble analyte bound to a solid phase particulate reagent which is not agglutinated, or washed to remove unbound component. This primary optical measurement is corrected, upon consideration of other optical measurements, for interferences caused by light scattering by the particles or the optical effects of extraneous components of the sample. Among the advantages of the present invention are that it does not require an eluting agent, it uses smaller quantities of particles than do minicolumns, it does not require removal of unbound constituents from the sample container, it requires fewer manipulation steps and volumetric measurements, and it lends itself to use of disposable sample handling devices in conjunction with standard microtiter plate readers. Because the method of the present invention requires fewer liquid manipulation steps, there is greater precision with reduced labor costs as compared to the conventional methods. It is an object of the present invention to provide rapid, simple, convenient and inexpensive methods for measuring proportions of one or more analytes in a sample, usable even by relatively unsophisticated personnel.

In one embodiment of the present invention, an affinity reagent, which binds the soluble analyte, is immobilized on particles, such as beads, to form a solid phase reagent. The particles must be substantially transparent, so as to minimize interference with the optical reading of the analyte while it remains bound to the solid phase reagent. These particles also are much larger than those typically used in agglutination assays, both to facilitate their sedimentation and to reduce their interference with subsequent optical measurements as a result of light scattering. Unlike a dipstick or test tube, a relatively small volume of particles can present a large surface area, and thus a large number of analyte binding sites. Preferably, the particles are porous, to further enhance analyte capture. As a result, the present assay is unlikely to run into the problem of saturation if the concentration of analyte is high.

This solid phase reagent is then incubated with a sample solution sufficiently long for the analyte to interact with the reagent. The mixture is then allowed to settle, or is centrifuged, so that substantially all of the particles segregate within one zone (the "particle rich zone") of the reaction vessel, leaving another zone substantially particle-free. It should be noted that the present invention does not require that the binding of the particle-bound affinity reagent to the analyte result in agglutinate formation; substantially all particles, whether bearing bound analyte or not, are transported to the "particle- rich zone."

As a result, substantially all of the analyte is bound by the particles and therefore concentrated in the particle-rich zone, whereas unbound soluble constituents of the sample are in substantially equal concentrations in the particle-rich and particle-free zones. If the volume of the particles is chosen to be small relative to the volume of the sample, the effect is to concentrate the analyte into a smaller volume, thereby enhancing the sensitivity of the assay.

Without the need for first washing unbound materials off the solid phase, or eluting the analyte from the solid phase, the quantity of analyte in the solid phase is then determined by optical means. This may be measuring : (1) the optical density of the particle-rich zone at a wavelength at which the analyte absorbs light; (2) light emission by the analyte at a wavelength at which, as a result of proper excitation, the analyte fluoresces or phosphoresces (or a wavelength at which the analyte quenches the fluorescence of a secondary reagent); or (3) some other optical property, at a wavelength at which the analyte exhibits or can be caused to exhibit a distinctive optical property. For the sake of convenience, the remainder of this summary will describe the invention as an absorbance assay, but it should be understood that the discussion applies, mutatis mutandis, to other forms of optical measurement suitable for the analyte in question.

The assay, as thus far described, is subject to a number of interferences which must be dealt with in order for the assay to be accurate. First, the particles can cause light loss. While some light loss is caused by absorbance, if the particles chosen are highly transparent at the wavelengths used in the assay, a more important factor is that the particles scatter light as a result of diffraction from the surface and internal refraction. The greater the number and the smaller the size of the particles, the greater the light loss due to scattering. This would cause the analyte reading to be exaggerated, if no correction were made.

To complicate matters further, the amount of scattering is affected by the amount of analyte captured by the particles through the affinity reagent.

Second, components of the sample other than the analyte may absorb light at the assay wavelength, thereby impairing with the correlation of analyte concentration with optical density. It is for this reason that many prior art assays wash unbound components off the solid phase.

Surprisingly, Applicants have discovered that by making certain control measurements, these interferences can be satisfactorily accounted for. In essence, and with certain exceptions discussed hereafter, Applicants measure both the sample and a "blank", at two different wavelengths, in both the particle-rich and particle-free zones.

For the purpose of the present invention, a "blank" is a control solution in an at least partially transparent container as similar as possible to that used to receive and examine the sample. Preferably, if the sample is blood, the control solution is a saline buffer. If the sample is pretreated to prepare it for analysis, the "blank" is treated in the same way. For example, if an anti-coagulant is added to a blood sample, it is also added to the "blank". The same particulate reagent is added to both the sample and to the "blank". Both the sample and the "blank" are centrifuged or allowed to settle so as to form particle-rich and particle-free zones. The "blank", of course, is free of both analyte and the other species endogenous to the sample, but is otherwise as similar as practical to the sample. It is not necessary to run a "blank" with every sample.

The sample and the "blank" are read at first and second wavelengths. The first wavelength is one at which the analyte strongly absorbs light. The reading at the first wavelength in the particle-rich zone of the sample is compared with the reading of the particle-rich zone of a "blank"

at the same wavelength. This allows for correction of the basic reading for the basal absorption and scattering of light by the particles in the absence of analyte. Unfortunately, this correction alone is not enough to account for all particle effects. Absorption of analyte by the particles increases the mass of the particles and therefore changes their optical characteristics, e.g., increasing the degree to which they refract light.

To correct for this effect, the particle-rich zones of both the sample and the "blank" are read at a second, control wavelength. This is a wavelength at which the analyte essentially does not absorb light, so that, to the extent that the particle-rich zone of the sample has a higher optical density than does that of the "blank", it is attributable to the analyte-induced change in light scattering by the particles but not to specific absorbance by the analyte, either bound or not. Applicants have found, empirically, that while, as could be expected, the effect of the analyte on light scattering can vary from one wavelength to another, the degree of variation is sufficiently small so that the proposed correction is adequate to correct for the analyte-dependent incrementation of light scattering by the particles at the first wavelength.

It is further within the contemplation of the invention, although not mandatory, to spread the particle-rich fraction into a relatively thin layer, so as to reduce multiple reflections.

As already alluded to, another potential source of error is absorbance of light at the first wavelength by unbound constituents of the sample which are present in the free volume of the particle rich zone. If this error were not corrected for, this absorbance would cause the amount of the analyte to be overestimated. The degree of light loss in the particle rich zone which is attributable to this source may be determined by measuring the absorbance at the same wavelength in the particle-free zone, and multiplying it by the free volume proportion of the particle-rich zone. The resulting product, which represents the light loss attributable to the absorbance of light by unbound constituents in the free volume of the particle-rich zone, is subtracted from the absorbance of the particle-rich zone. This correction relies on the fact that both the particle-free zone, and the free volume of the particle rich zone, should contain the unbound constituents in equal concentrations.

One must also consider the nonspecific loss of light through absorbance, reflection or refraction by the optical train and the walls of the container for the sample and the "blank". This is accounted for by the optical reading of the particle-free zone or the "blank" at either the first or the second wavelength. It is not necessary that readings be taken at both wavelengths.

There may also be differences in nonspecific absorbance between the container of the sample and the container for the "blank". In the case of a capillary-type container, these may be attributable, for example, to differences in inside or outside diameter, longitudinal straightness, cross-sectional roundness, or cleanliness. Measurement of the light loss in the particle-free zone of the sample at the second wavelength provides a basis for correction for these interferences, as will be explained hereafter.

The present invention is also well suited to analyzing for more than one analyte at one time, for example, both glycated hemoglobin and unglycated hemoglobin. In this embodiment of the assay, one analyte is preferably bound by the affinity reagent, and so is concentrated in the particle rich zone, and the other is not, and therefore may be found in the particle free zone. Both analytes are measured optically.

For example, the glycated hemoglobin may be bound by an affinity reagent which is sugar-specific (e.g., a boronate compound), and the first wavelength may be one at which hemoglobin (whether or not glycated) absorbs light strongly. The reading in the particle-rich zone of the sample will be indicative of the level of glycated hemoglobin, and the reading in the particle-free zone of the sample will be indicative of the level of unglycated hemoglobin, after corrections such as those already indicated.

Hemoglobin absorbs strongly in the "blue" (400–420 nm) and "green" (540–570 nm) regions of the spectrum. While any wavelength from 400 to 590 nm may be used for detecting hemoglobin, 560 nm is preferred. On the other hand, hemoglobin does not significantly absorb light in the "red" region (630–690 nm). Any wavelength in this "red" region may thus be used as the control wavelength. Any absorbance at this red wavelength will be due to unintended variations in the optical path, and thus is not due to the presence of hemoglobin.

In the above example, both analytes (hemoglobin and glycohemoglobin) absorbed light at the same wavelength, and they were distinguished by their differing affinity for the solid phase reagent. However, it is possible that the analytes will absorb light at different wavelengths, in which case the sample will be read at each of the wavelengths characterizing one of the analytes. If desired, all of the analytes may be concentrated into the particle rich zone by use of either a single affinity reagent which binds all of the analytes, or a mixed affinity reagent whose components are collectively, if not individually, capable of binding all of the analytes. Alternatively, some of the analytes may be allowed to remain in the particle-free zone. In any event, there is no need to separate the analytes from each other by affinity to different particles in the system.

Other embodiments of the present invention are also disclosed herein. The affinity reagent may be provided in soluble form, provided that the particles are chosen so that the affinity reagent:analyte complex will tend to be excluded from the pores of the particles, hence causing the concentration of analyte to be higher in the particle-free zone than in the particle-rich zone (the reverse of the partitioning achieved by a particle-bound affinity reagent). The assay may be conducted in a competitive format, where the analyte competes with an analyte analogue for the affinity reagent and either the analyte analogue is labeled, and the affinity reagent coupled to the particles, or vice versa. Fractionation (and the use of a "blank") can be dispensed with if measurements are made at two additional wavelengths at which the particles block light, but at which the analyte has contrasting degrees of absorbance or fluorescence.

Figure 1:
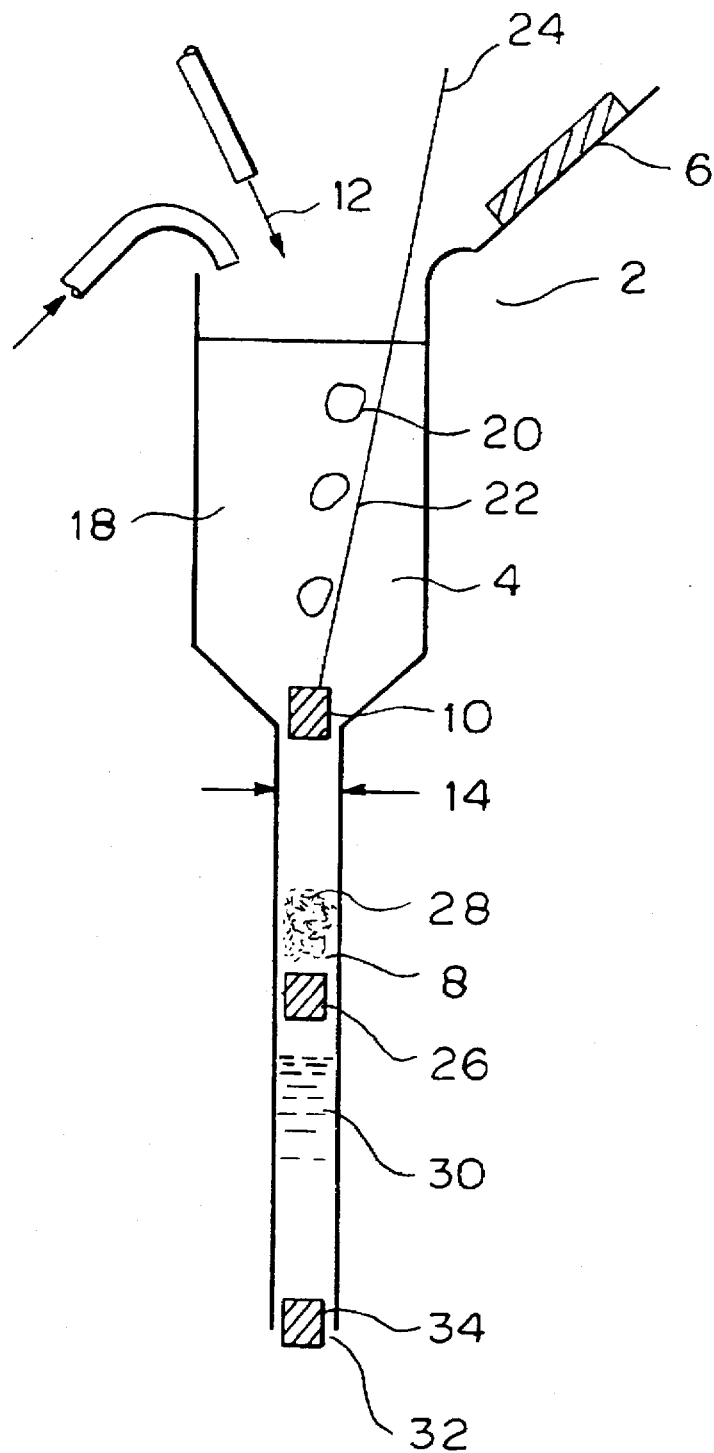
FIG. 1 shows the combination of a reaction chamber with a long, thin tube in a single assembly.

FIGURE ELEMENTS 2. reaction/measuring apparatus
4. reaction chamber
6. cap
8. optical measuring container
10. plug separating insides of two chambers
12. sample
14. bore
18. mixing means
20. bubbles
22. bottom of reaction suspension
24. string attached to plug
26. frit in measuring chamber
28. particles
30. liquid
32. bottom of measuring chamber
34. closure for bottom of apparatus
36. optical path for particle-rich fraction
38. optical path for particle-free fraction
50. light emitting diode
51. light emitting diode
60. parallel optical trains
62. alternate optical path

DETAILED DESCRIPTION OF THE PREFERRED EMBODIMENTS OF THE INVENTION

Types of Assays

In one embodiment, the analyte is captured by the particles as a result of an affinity reagent bound to the particles, and is thus concentrated into the particle-rich zone.

Many analytes will be intrinsically detectable as a result of their characteristic absorbance (e.g., glycohemoglobin and normal hemoglobin at 560 nm) or fluorescence (e.g., riboflavin).

If the analyte is not intrinsically detectable, it may be detected indirectly by a variety of means:

(1) if the analyte is capable of modulating the optical properties of a marker molecule in a concentration-dependent manner, the latter may be added (before, during or after particle addition) to the sample as a secondary reagent, and then the "marker" can be read. For example, hemoglobin can quench the fluorescence of certain fluorophores.

(2) the analyte may be specifically labeled, covalently or noncovalently, with an optically detectable label. One manner of labeling would be to incubate the sample (before, during or after particle addition) with a conjugate of a label and an affinity reagent, (which may be, but need not be, the same affinity reagent used to bind the analyte to the particles).

(3) the assay may be conducted in a competitive format, that is, the analyte is allowed to compete with a known amount of an optically detectable analyte analogue. The greater the amount of analyte analogue detected in the particle-rich zone, the less the amount of analyte in the sample. While this format is of greatest interest where the analyte itself is not optically detectable, there may be advantages to using a competitive assay even when the analyte could be "read" directly.

In another embodiment, the affinity reagent, rather than being attached to the particles, is added in soluble form to the solution. After joining of analyte and affinity reagent in solution, the analyte molecules will tend to be excluded from the internal volume of the particles and will be present in higher concentration in the particle free zone. Again, secondary reagents, such as modulatable markers, labeled affinity reagents, and analyte analogues may be used as necessary or desirable. If analyte analogue is used, the soluble affinity reagent is labeled, and the analyte analogue is conjugated to the particles. This allows for competition of bound analyte analogue and soluble analyte for the labeled affinity reagent.

Samples

The sample solutions of the present invention may be a biological fluid, such as blood, urine, sweat, tears, milk, amniotic fluid or cerebrospinal fluid, or a nonbiological fluid such as a beverage, groundwater, or a solubilized soil sample, which could contain the analyte(s) of interest. The samples may contain minor amounts of particulate matter which do not substantially interfere with the assay. The sample may be manipulated, chemically or mechanically, to prepare it for analysis by the present method.

Analyte

The analytes may be any soluble (incl. solubilizable) analyte which is susceptible of detection by the methods described herein. Among these analytes are proteins such as hemoglobin, glycosylated hemoglobin, albumin, immunoglobulins and enzymes; lipids, such as triglycerides and lipoproteins, including high-density and low-density lipoproteins; therapeutic drugs, such as diphenylhydantoin, phenobarbital, tobramycin, lidocaine, procainamide, and the like; natural or synthetic steroids such as cortisol, aldosterone, testosterone, progesterone, estriol, etc.; hormones, such as thyroid hormones, peptide hormones, insulin; antigens, antibodies, and other species which react naturally with a receptor.

At least one of the analytes to be assayed in a given assay will be one for which an affinity reagent, as hereafter defined, is available, so that it can be concentrated into the particle-rich zone. If two or more analytes are to be assayed simultaneously, the remaining analytes may be, but need not be, similarly captured.

Preferably, the analyte will have one or more characteristic wavelengths of absorbance or fluorescence, or some other optical characteristic, by which it can be distinguished from the other constituents of the sample. If the intrinsic optical characteristics of the analyte are insufficient to differentiate it from other sample constituents, the analyte may be labeled to confer a suitable optical characteristic upon it.

The method of the present invention may be used to measure an analyte, based on any optical characteristic of the analyte, or of a label specifically bound to the analyte, which helps to distinguish it from one or more of the other constituents of the sample. Examples of suitable characteristics are set forth below. In general, the choice will depend on the signal-to-noise ratio (the contrast there is between the intrinsic absorbance, fluorescence, etc., of the analyte (or of the intended label) and that of the potential interfering constituents of the sample), the sensitivity required for the assay (given the typical levels of the analyte and the interfering constituents in the expected samples), and the availability of the appropriate optical apparatus.

Absorbance. An analyte (or label) may specifically absorb light at certain wavelengths, in effect converting the incident electromagnetic energy into other forms, such as heat. If light of such a wavelength is directed through the sample, the amount of light loss will depend, in part, on the concentration of the analyte in the sample.

The absorbances of a great many compounds are known, and one skilled in the art can readily determine at what wavelengths assays should be conducted for any particular analyte in order to optimize the results. Many handbooks and textbooks give absorption peaks for a number of compounds, e.g., *Handbook of Fluorescent Probes and Research Chemicals*, 5th edition, 1991–1994, Haughland, ed., Molecular Probes, Inc., Eugene, 1992. This particular handbook shows absorption peaks for reagents as well as absorptions for many chemicals available as fluorescent probes.

The optical apparatus required for an absorbance assay would be a light source, a light sensor, and a filter.

Fluorescence. An analyte (or label) may, when excited by light of one wavelength, emit light of a longer wavelength. The apparatus required for a fluorescence assay is similar to that required for an absorbance assay, however, the light source will normally radiate in the blue or ultraviolet region of the spectrum.

Fluorescence Quenching. The analyte (or a label) may quench (reduce) the fluorescence of a second molecule, which may be either endogenous or exogenous to the sample. The optical apparatus required is similar to that for a direct fluorescence assay, however, the assay may require use of a quenchable fluorophore as a secondary reagent.

Refractive Light Loss. Transmitted light may change direction as it passes from one medium to another, a phenomenon known as refraction. As a result of the action of the affinity reagent, the particles of the present invention will acquire a deposit of analyte. The degree of refraction at the particle/solution interfaces will depend on the amount of analyte collected inside the particle as a result of affinity attraction. Refraction can result in light loss, if the light is directed away from the detector. Different substances cause different degrees of refraction, so the degree of refractive light loss can be indicative of the amount of analyte present.

This technique is especially useful when the constituent to be measured has no color contrast which can be detected with simple instruments.

Refractive light loss may be used to measure total antibody gamma globulin. Protein A is attached to a particle such as 4% crosslinked beaded agarose. The attachment of gamma globulin to the particle-bound protein A is sufficient to cause a change in the refractive index of the particles, and thereby provide a loss of light which is proportional to the amount of gamma globulin attached to the particles.

Refractive light loss may also be used as a measure of glycoalbumin.

The amount of refraction may vary as a function of wavelength, lending to a dispersion of light of different wavelengths along different paths when white light is refracted.

Analyte Analogues

An analyte analogue is a reagent which is capable of competing with the analyte in the sample for the binding/reaction sites of the affinity reagent. It may be, but need not be, identical to the analyte. If not intrinsically optically detectable, it may be extrinsically labeled for this purpose.

Labels

A label is a chemical entity which, when conjugated to another substance, renders the latter more readily detectable by optical means. Typical labels include fluorophores and chromophores, with fluorophores normally being preferred.

Preferred fluorescent (including fluorophore-forming) labels include anthracene-2,3-dicarboxaldehyde (emits at 475 and 546 nm), naphthalene-2,3-dicarboxaldehyde (520), fluorescamine (478), and related compounds, which react with primary amines to form fluorophores, as well as fluorescent chelates of aluminum, zinc and rare earth elements.

Morin, an ion binding compound, is of interest because it is both a dye and a fluorophore (changing color with different metal ions), and competes for binding to boronate affinity reagents, and so can act also, in certain assays (e.g., assays for hemoglobin or glycohemoglobin), as an intrinsically labeled analyte analogue.

A label may be attached to an analyte, analyte analogue or affinity reagent by the methods discussed under "Conjugation", infra.

Affinity Reagent

The affinity reagent may be any molecule which has a greater affinity for the analyte than for one or more of the other constituents of the sample. The principal classes of affinity reagents include lectins (where the analyte contains carbohydrate), carbohydrates (where the analyte is a lectin), antibodies (where the analyte is an antigen), antigens (where the analyte is an antibody), enzymes (where the analyte is an enzyme substrate or inhibitor) and enzyme substrates and inhibitors (where the analyte is an enzyme). (In the enzyme context, it may be desirable to inactivate the enzyme without abolishing its binding activity). Charged or hydrophobic substances have also been shown to be useful as affinity reagents.

Table I provides some examples of analytes detectable with particular affinity reagents.

TABLE I

| Affinity on particle | Linker | Analyte(s) | Method of Measurement |
|---|---|---|---|
| Boronyl group | | glycated vs non glycated | |
| | | a) hemoglobin | a) Absorbance 570 nm; Fluorescence quench |
| | | b) globin | b) Refractive light loss |
| | | c) albumin | c) Refractive light loss |
| | | riboflavin | d) Specific fluorescence on particulate |
| Specific Antibody | | Hemoglobin A1c | Absorbance at 570 nm |
| | | Non Light Absorbing Antigen | Refractive light loss |
| Carbohydrate with free OH on adjacent carbon | Homodimer of boronyl | a) glycohemoglobin | a) absorbence at 570 nm |
| | | b) riboflavin | b) fluorescence |
| Carbohydrate with free OH on adjacent carbon | Heterodimer a) boronyl | | Competitive assay using fluorescent analyte analogue |
| Protein A | b) lectin Specific Antibody | Blood group substances Transferrin | Render transferrin fluorescent by labeling |

Particles

The particles used in the present invention must be compatible with both the affinity reagent and the sample, and it must be possible to immobilize the affinity reagent onto the particle. The particle must be sufficiently transparent to permit the detecting of contrast attributable to the presence of the analyte.

The particles used are transparent in some media. However, when the particles are immersed in the reaction medium, there is always some surface refraction because of a mismatch in the index of refraction between the solution and the particles. This phenomenon is demonstrated by the Sephadexes, including Sephadex G10, 25, 50, 75, 100 and 200, which have a swollen solid mass of approximately 25, 20, 9, 6, 5 and 2.5% solids, respectively. Transmission of 560 nm light through these particles in capillaries, expressed as a percentage of transmission through the particle-free zone, is 7.2, 32.4, 78.3, 73.1, 84.4 and 89.9%, respectively. Transmission at 630 nm is 8.1, 33.9, 77.7, 74.2, 86.6 and 91.7%, respectively. (Sephadex G75, in which the transmission may seem anomalous when compared with the others, is composed of smaller spheres.) When it may be done without interfering with the assay, a refractive index-adjusting agent may be added to the medium to reduce refractive light loss.

The transparency of the particles used to incident light used for assay must be such that differences in transmission or fluorescence attributable to differences in analyte concentration, are readily measurable at the desired wavelength. This degree of transparency is hereinafter referred as "substantially transparent". This is the essential criterion for the particles to be used in each assay. Preferably, the particles are about equally transparent to light at the detection and control wavelengths.

Many different types of particles can be used, including carbohydrates, polystyrene or other plastics, and other substantially transparent (and preferably porous) particles. The preferred particles are carbohydrates such as dextran, agarose, agar, deacetylated chitin, or starch. Agarose and dextran are especially preferred. These particles may form free standing gels or may require crosslinking with crosslinkers such as epichlorohydrin or glutaraldehyde.

Conveniently, the particles are in the form of beads which are roughly spherical, having a diameter of from about 10 to about 400 microns, more preferably, 20 to 200 microns. Porous particles are preferred. The porosity of the particles may range from about 10% to about 99% of the volume of the particles; a porosity of more than 90% is preferred.

On occasion the particle itself may serve as an affinity reagent, e.g., a particle formed from a carbohydrate polymer which is used in an assay for a lectin analyte.

Conjugation

An affinity reagent may be conjugated directly or indirectly, covalently or noncovalently, to a particle, thereby forming a "solid phase" or "participate" reagent, or to a label, to form a labeling reagent. More than one affinity reagent may be immobilized on the same or different particles. Among the compounds that can be used to covalently attach the affinity reagent are paranitrophenyl chloroformate, cyanogen bromide, glutaraldehyde, epoxy groups, divinyl sulfone, epichlorohydrin, and others, provided the crosslinking agent is suitable for the specific application. For noncovalent conjugation, the binding may rely on antibody:antigen, lectin:sugar, avidin:biotin or other specific binding pairs, and the conjugation partners may be tagged with opposite members of a binding pair to facilitate such binding. Of course, whatever the mode of conjugation, the affinity reagent must still be able to bind the analyte.

These conjugation techniques may also be used, mutatis mutandis, to conjugate a label to an analyte, analogue, or affinity reagent, or an analyte analogue to a particle.

Incubation

The purpose of incubation is to expose the sample to the affinity reagent until an equilibrium is reached for the attachment of an analyte to the affinity reagent on the particle. Mixing can reduce the time necessary to reach equilibrium. Turbulence may be supplied to the system by tumbling or shaking the container, or by passing bubbles through the reagent-sample mix. In the case of bubbles, this type of mixing may be begun before sample is added to the system. The optimum incubation period is related to the degree of specific affinity of the reagent for the analyte, as well as to the quantities of reagent and analyte present. Typically, the incubation is for about five to ten minutes.

Preferably, the ratio of the volume of the particles to the volume of the sample is less than 1:1, more preferably less than 5:1. This has the affect of concentrating the analyte into a smaller volume and hence increasing the sensitivity of the assay.

When the assay is for two analytes, one of which is to be detected in the particle-rich zone and the other in the particle-free zone, the aforementioned volume ratio is desirably similar to the mean ratio of their concentrations in the samples. For example, in the GHb/Hb assay, unglycosylated Hb is about 10 times as prevalent as GHb. If the ratio of particle volume to sample volume is, say, 1:9, the absorbance at 410 nm for Hb in solution and GHb in the particles will be of about the same order of magnitude.

A precise ratio of particles to solution in the reaction vessel may be provided in an assay kit so that the proportions of the partition become known, and the volumes of particles and solution need not be precisely transferred to the measuring vessel.

Incubation and fractionation may be carried out in the same or different vessels.

Fractionation

After incubation, the mixture is fractionated within a single reaction vessel into a particle-rich zone and a substantially particle-free zone. The substantially particle-free fraction is sufficiently free of particles so that any particles in the substantially particle-free zone do not detectably refract light transmitted through this particle-free zone. The fractionation may be effected merely by permitting the particles to settle to the bottom of the reaction vessel under the influence of gravity, or the suspension may be centrifuged to hasten the fractionation.

A typical fractionation time under normal gravity is about ten to fifteen minutes. Alternatively, a one to three minute centrifugation at about 500×G provides essentially immediate constant readings which compare favorably to 10–15 minutes of settling.

As a further alternative, the particles may be collected on a filter, such as a polypropylene frit, inside the reaction vessel, that allows liquid to pass but collects the particles. The particles therefore remain on one side of the filter.

Apparatus

The present invention is not limited to any particular apparatus.

While it is possible for the optical reading to be conducted in the same container in which the incubation and fractionation occurred, the use of two separate containers is desirable. For fractionation, use of a wide bore container will improve circulation and hence facilitate fractionation. For optical reading, use of a narrow bore container will shorten the light paths and hence reduce light loss due to scattering. The containers may be of any shape, however, cylindrical containers are preferred.

The incubation, fractionation and measurement steps may be performed manually or automatically. If automatic, means are preferably provided for introducing the sample and reagents into the "reaction vessel", and for transferring the fractionated contents, with as little disturbance as possible, to the "optical measuring vessel" (usually a capillary). If desired, means can be provided for agitating or centrifuging the mixture.

Figure 2:
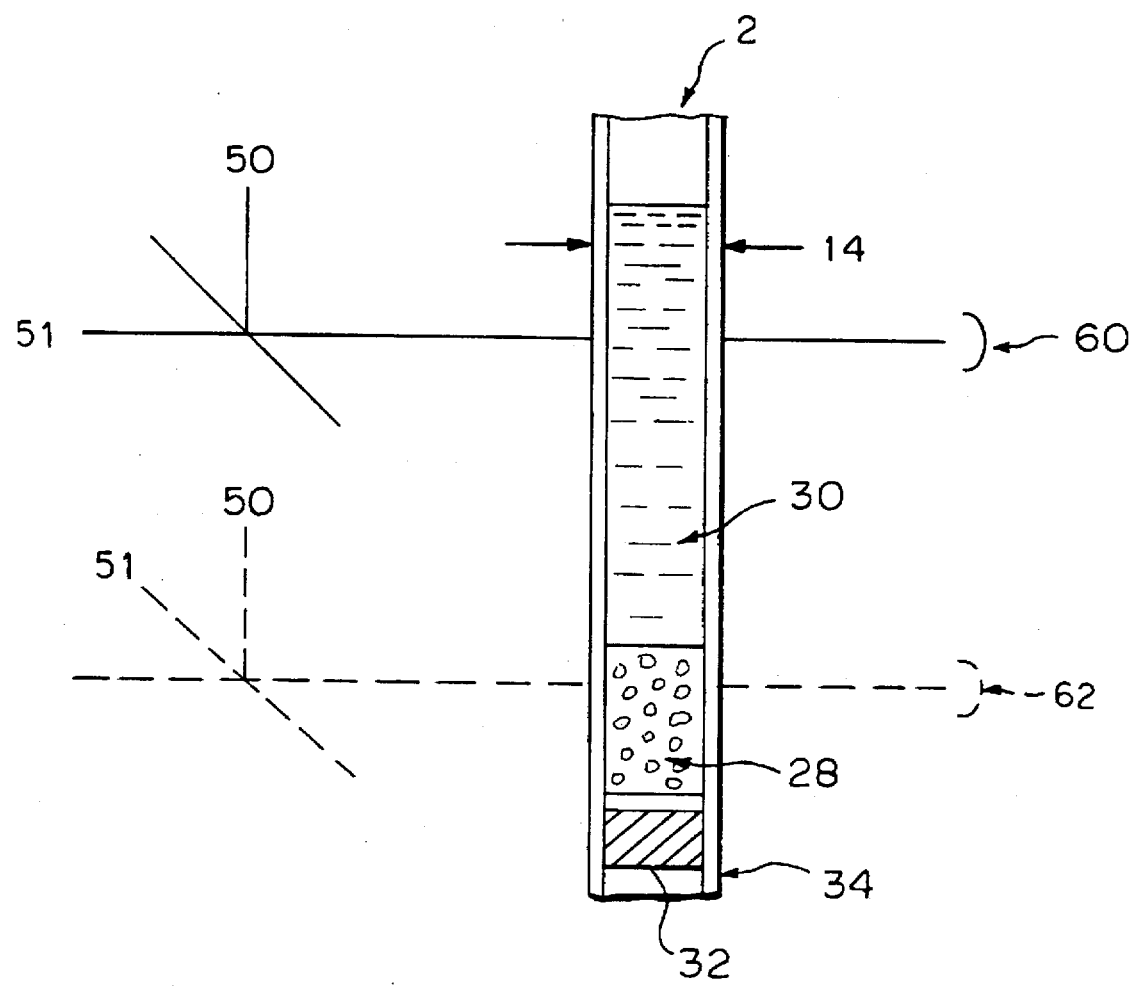
FIG. 2 shows a long, thin tube using either a photodiode or LED for assays.

A preferred apparatus for use in the present invention is shown in FIGS. 1 and 2. The apparatus (2) comprises a reaction chamber (4) having a cap (6) which may be opened but which is liquid tight when closed. The cap (6) may be attached by a loop of plastic material to the reaction chamber (4). The bottom of the reaction chamber (4) is cone shaped and is connected to the measuring container (8) so that the hollow insides are continuous. A plug (10) separates the inside of the two chambers during storage and when sample (12) is first inserted into the reaction chamber (4). The reaction chamber (4) is conveniently made of a light-weight unbreakable plastic material such as polypropylene. However, the exact composition of the material of the reaction vessel is not important, as long as the material can be molded to proper shape and is chemically inert to the reactants.

The optical measuring container (8) may be made of any optically transparent material such as plastic or glass. Glass is preferred, unless the plastic is of assured optical quality. The bore (14) may be round or may have parallel sides, although a round bore is preferred. The bore is generally between about 1 mm and 3 mm, but more preferably, 1.2 to 2 mm. The most preferred bores are about 1.6 mm in diameter. Of course, the ultimate bore size is determined by the refractile characteristics of the particles in the liquid. Where the refractive index of the particles closely matches the refractive index of the solution, the preferred bore may be greater than 1.6 nm. The bore (14) must be of known geometry for the length of the measuring container (8).

A mixing means, here portrayed as a small plastic air tube (18) providing positive pressure to the reaction chamber (4), supplies bubbles (20) to the bottom of the reaction suspension (22) during the mixing time. As the bubbles (20) rise, turbulence is created, providing the required mixing action. At the end of the mixing period, the plug (10) is pulled by means of an attached string (24), thus providing continuity between the reaction chamber (4) and the bore (14) of the measuring chamber (8). Liquid suspension (22) then settles into the measuring chamber and is stopped from exiting by a tightly fitting frit (26) inserted part way on the length of the measuring container (8). The frit (26) retains the particles (28) but permits passage of liquid (30). The precise additional pressure required to initiate flow of liquid (30) past the frit (26) and to stop before exiting the bottom (32) of the measuring chamber (8), is supplied by closing the cap (6).

To ensure that no liquid leaks from the bottom (32) of the capillary (8), a closure (34) may be provided. Optionally, the reaction chamber (4) can be separated from the measuring container (8).

The optical paths for the particle-rich fraction (36) and for the particle-free solution (38) are defined at positions along the measuring container by the position of the frit.

Alternatively, a source of positive pressure (18) may be supplied through the measuring tube (8) which is opened to the mixing chamber before sample is added therefor. Thus, bubbles (20) are supplied to the mixing chamber (4) through the measuring tube (8). At the end of the mixing period, the pressure is reversed and both particles and solution settle into the measuring tube (8).

Alternatively, the reaction chamber (4) and the optical measuring container (8) may be separated from the inception of the procedure, and means for transferring a portion of both particles and solution is provided. Such means may be a precisely metered negative pressure displacement device, such as a pipette. In this case, a closure (34) for the bottom of the optical measuring container (8) is required.

The invention is not limited to any particular method of making the disclosed optical measurements, or to any particular apparatus therefor. One means for reading the results obtained using the method of the present invention is a narrow slit transmission of white light through a capillary with a slit and a narrow range of filters before an optical sensor (photodiode). The Becton Dickinson QBC Autoread is one example of this type of device, and Example 1 provides data obtained with this instrument.

In another type of device narrow slit excitation light, white light is the source with a narrow band filter, while the fluorescent analysis is with broad band light filters. This is the standard BD Autoread with no modification of filters.

In a broad slit white light source which scans multiple (e.g., 12) parallel capillaries at one reading, the white light source is wider than the capillary and the capillaries are each laid into a slot which limits transmission of light around the capillary. This is a microtiter plate reader adapted to read capillaries. Alternatively, a reader can be used which reads fluorescence instead of transmission.

In another type of reader, the capillary is surrounded by a cylindrical lens. The lens accepts a broad, parallel light beam which is focused onto the capillary through which the light is transmitted. As light exits, the light is spread again into a broad parallel beam. The light for this assembly is two narrow band light emitting diodes, 50, 51 of which one (50) provides light in the 560 nm range and the other (51) in the 635 nm range. This system is manually positioned to read first the particle-rich zone and then the particle-free zone. An alternate optical path is shown at 62.

Alternatively, this system may feature two parallel optical trains 60 which read simultaneously as the bottom of the capillary triggers a microswitch upon insertion. In this design, a microprocessor controls the on-off switching of light emitting diodes and computes the results. Thus, results are obtained immediately upon inserting and removing the capillary.

Use of Optical Data

Optical densities may be used to calculate analyte concentrations by hand, or with the aid of a calculator, nomograph, or computer. To illustrate how the optical data may be used to derive an assay result, we will explain its use in calculating "% GHb". The definition of this value is:

$$GHb\ \% = 100 * (Amt\ GHb)/(Amt\ GHb + Amt\ Hb),$$

where the "Hb" refers to unglycated hemoglobin only.

If the amounts were being inferred from the true optical densities (O.D.'s) of GHb and Hb in fractions of different volume, the volumes of GHb and Hb fractions would need to be taken into account, as follows:

$$GHb\ \% = 100 * \frac{(vol\ GHb * OD\ GHb)}{(vol\ GHb * OD\ GHb) + (vol\ Hb * OD\ GHb)}$$

The optical density of an object is log $(I_o/I)$, where $I_o$ is the intensity of the incident ray and I is the intensity of transmitted ray.

Dividing by vol GHb, we get $$GHb\ \% = 100 * \frac{OD\ GHb}{OD\ GHb + OD\ Hb * \frac{(vol\ Hb)}{(vol\ GHb)}}$$

If the hemoglobin were found only in the particle-free zone, and the glycohemoglobin only in the particle-rich zone, the volume ratio in the denominator, vol Hb/vol GHb, is in effect the ratio of the volume of the solution to the volume of the particles, which is a constant for a particular assay system. It may be considered a "dilution factor" (DF). The DF is preferably in the range of 5–20, and more preferably is about 9.

The optical density of the particle-rich zone is the sum of the optical densities of (a) the glycohemoglobin bound by the particles; (b) the particles themselves (either intrinsically or as a result of added mass of the analyte); (c) unbound constituents, including unglycated hemoglobin, in the "free volume"; and (d) the container holding the sample. Therefore, the optical density of the bound glycohemoglobin is the nominal optical density of the particle-rich zone less the optical densities of the particles, the free volume constituents, and container. (The optical density of the particle-free zone is the sum of the optical densities of (a) the glycated hemoglobin, (b) other unbound sample constituents, and (c) the container.)

The container affects all optical measurements, and can be accounted for by using a net OD, rather than a raw OD, in our calculations. In a glycohemoglobin assay, the net OD could be the $OD_{560} - OD_{630}$, since hemoglobin (glycated or not) absorbs at 560 nm but not at 630 nm. Let Sg=net OD of sample through gel (particle-rich zone);
Ss=net OD of sample through solution (particle-free zone);
Bg=net OD of blank through gel
Bs=net OD of blank through solution
FV=free volume ratio
DF=dilution factor
If so, then $$\% \ GHb = \frac{100 \ [(Sg - Bg) - (FV * (Ss - Bs))]}{DF \ (Ss - Bs) + (Sg - Bg)}$$

The dilution factor is a constant which will modify one or more components of the assay, depending on the method. It may also be replaced by a standard curve for purpose of final calculation. Like the dilution factor, the free volume ratio (FV) is a constant for a particular assay system.

The free volume is the volume of the particle-rich zone which is penetrable by the solution. This includes both the interstitial spaces between particles, and the volume of the pores inside the particles. The free volume ratio is the ratio of the free volume to the total volume of the particle-rich zone, which is the sum of the free volume and the solid volume of the particles. The free volume ratio must be less than 1.0, since some space is occupied by the solid matrix of the particles. However, since the preferred particles are highly porous, it is usually in the range of 0.7 to 0.98.

Free volume may be determined for a particular choice of particulate reagent and container by examination of a reference system. In the reference system, the particulate reagent is added to the same buffer as would be used in the "blank". A known quantity of an optically detectable marker molecule, which is not bound by the particulate reagent, is added to the reference system, and, at a wavelength at which the marker absorbs light, optical measurements are made in both the particle-rich and particle-free zones.

The optical density of the buffer solution, if the marker were its only light absorbing component, would be of the form $d^L$, where d was the optical density of the buffer solution measured along a light path of unit length, and L was the actual length of the light path. The optical density of the particle-free zone, which is entirely buffer solution, follows this formula. The optical density of the particle-rich zone, if no light were lost owing to absorbance or scattering by the particles, would be $d^P$ where P was the portion of the light path through the particle-rich zone which passed through the buffer in the free volume. The ratio P/L is equal, on average, to the ratio of the free volume of the particle-rich zone to the total volume of the particle-rich zone. Thus, the latter ratio, which is FV, can be determined from the optical densities of the particle-rich and particle-free zones in the reference system. Of course, since in practice there is absorbance by the container, and absorbance and scattering by the particles, one would correct for these interferences by using a net OD (which is the OD at the wavelength at which the marker strongly absorbs light, less the OD at a control wavelength), rather than the raw OD at the "marker" wavelength.

It is not necessary that FV be determined anew for each sample.

In our assay for glycohemoglobin, our preferred marker is unglycated hemoglobin. For one assay system, the dilution factor DF was 9 and the free volume ratio FV was 0.94. Assume that the following readings were made:

|  | Blank | Sample 1 | Sample 2 | Sample 3 | Sample 4 | Sample 11 | Wave length |
|---|---|---|---|---|---|---|---|
| Solution | .123 | .264 | 339 | .430 | .446 | .571 | 560 |
| Gel | .315 | .553 | .659 | .774 | .818 | .954 | 560 |
| Solution | .122 | .136 | .131 | .146 | .142 | .153 | 630 |
| Gel | .284 | .320 | .318 | .332 | .347 | .345 | 630 |

Subtracting the reading at 630 nm from the readings of 560 um, the following is obtained:

| Difference Readings | | | | | | |
|---|---|---|---|---|---|---|
|  | Blank | Sample 1 | Sample 2 | Sample 3 | Sample 4 | Sample 11 |
| Solution | .001 | .128 | .208 | .284 | .304 | .418 |
| Gel | .031 | .233 | .341 | .442 | .471 | .609 |

Calculating the % GHb sample 1

$$\text{Observed value} = \frac{100 \ [(.233 - .031) - (.94 \ (.128 - .001))]}{9 \ (.128 - .001)}$$

Observed value=6.2%

Similar calculations could be made on the other samples.

These values are likely to differ from those calculated by other methodologies. To make the values more comparable, GHb % may be calculated by the present method for a "high calibrator" solution and a "low calibrator" solution, for which GHb % has been determined by an alternative method. The GHb % results for the calibrators, as calculated by both methods, are compared. Sample GHb % as calculated by the present method may then be rescaled for comparison to values derived by the alternative method.

The following examples are provided to illustrate the present invention, and are not to be construed as limitations.

EXAMPLE 1

Glycohemoglobin by Optical Absorbance

In this example, a direct assay for glycohemoglobin is made in which a sugar binding boronic compound is used to capture the analyte, which is subsequently measured by its characteristic absorbance. The affinity reagent used was aminophenyl boronate, and this was attached through a spacer arm to microbeads made up of crosslinked 6% agarose gel. The resin was washed with water, and was finally washed with Reagent A. Reagent A was prepared by raising the pH of a 0.27M ammonium acetate buffer which contains 0.05M magnesium chloride to pH 8.0 by adding concentrated ammonium hydroxide. A precise proportion of 1 part settled resin to 9 parts Reagent A was transferred to reaction vessels which were closed by caps for storage. The total fill was approximately 450 µL for each reaction vessel.

Approximately 10 microliters of whole blood hemolysate was pipetted into a reaction vessel which contained Reagent A. The reaction vessel was then closed and mixed by rotation for approximately five minutes.

At the end of the mixing time, a portion of the reaction mixture, containing both resin and sample, was transferred to an optical measuring capillary, which was then closed at its bottom and gently tapped to eliminate bubbles. This was a round capillary, 75 mm in length, with an inside diameter of 1.6 m. A closure was supplied for one end of the capillary. The capillary was made to stand upright so that the resin settled to the bottom. The settling may be accelerated by centrifugation; however, the resin reached a constant level of compaction without centrifugation, in about 10 minutes.

Optical transmission readings were taken at 560 nm and 630 nm in both the particle-rich and particle-free zones. These measurements may conveniently be made with a microtiter plate reader using a plate adaptor to hold twelve parallel capillaries. Each capillary occupies eight well positions of an 8×12 or 96 well plate.

To complete the calculations, measurements are made on a blank reagent capillary containing the particle/reagent A mixture, but to which no sample has been added, and, for calculating FV, another reagent capillary containing a hemoglobin sample with no glycohemoglobin. The measurements are merely a calibration to provide constants to the calculation, and need not be performed concurrently with each sample.

For convenience, the calculations in this example were made on the measured optical density output of a microtiter plate reader. Of course, it will be obvious to those skilled in the art that the initial measurements are electrical, such as in millivolts, which are then converted to optical density values by the instruments.

The glycohemoglobin attached to the resin is calculated from the sample measurement:

$$GR = OD\ resin - (FV \times OD\ solution)$$

and the proportion of glycohemoglobin to total hemoglobin is calculated from the sample measurements as $$GHb = GR/[OD\ resin + (9 \times OD\ solution)]$$

Finally, an adjustment is made for refractive light losses through the resin at the nonabsorbing wavelength (630 nm). This adjustment is characteristic for each type of measuring instrument, and depends primarily on the numerical aperture of the light collection lens in front of the light sensor. Conversion from proportion to percent is also accomplished in this final calculation:

$$GHb\ \% = 100 \times GHb - (A \times GR)$$

A is the adjustment, which is usually a negative number. Thus, calculation of GHb % without applying A as an adjustment usually yields an underestimate for GHb %.

Figure 3:
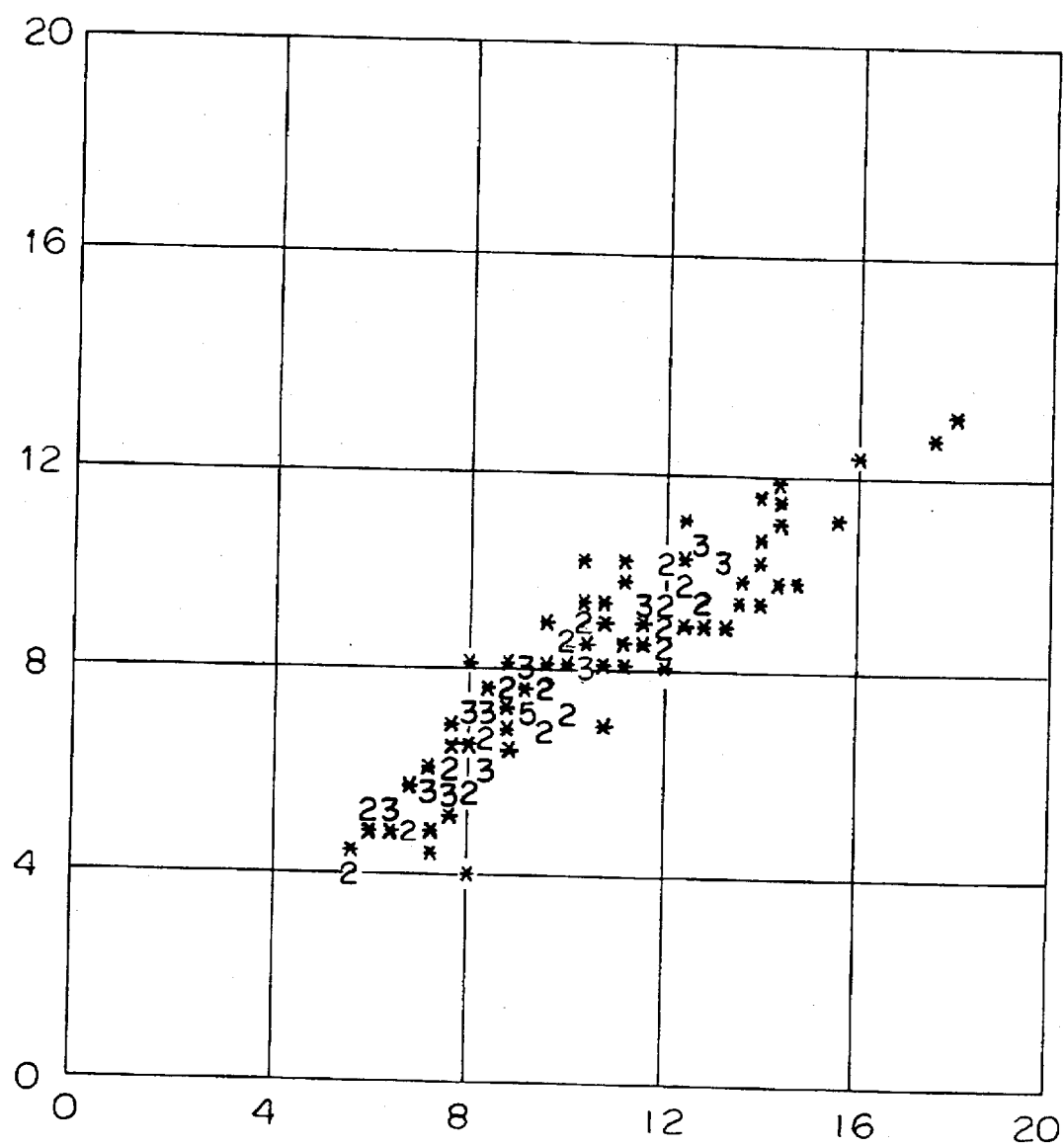
FIG. 3 shows a comparison of results obtained in Example 1 of to the present invention as compared to a standard commercial method (Helena Labs) for testing for glycohemoglobin.

(a) Readout With Microtiter Plate Reader, and LED Light Source 130 whole blood samples taken from diabetic patients as well as nondiabetic controls were subjected to the above procedure and calculation. The results are shown in FIG. 3 as compared to a standard commercial method of testing for glycohemoglobin (Helena Laboratory Columnmate).

(b) Readout With Custom Light Source and Reader

The same samples and capillaries as described earlier were again read in a modified Becton Dickinson QBC Autoread (7 Loveton Circle, Sparks, Md.), where the light source, originally a red LED, was replaced by a halogen tungsten lamp, and filters for 560 nm and 630 nm were supplied.

Figure 4:
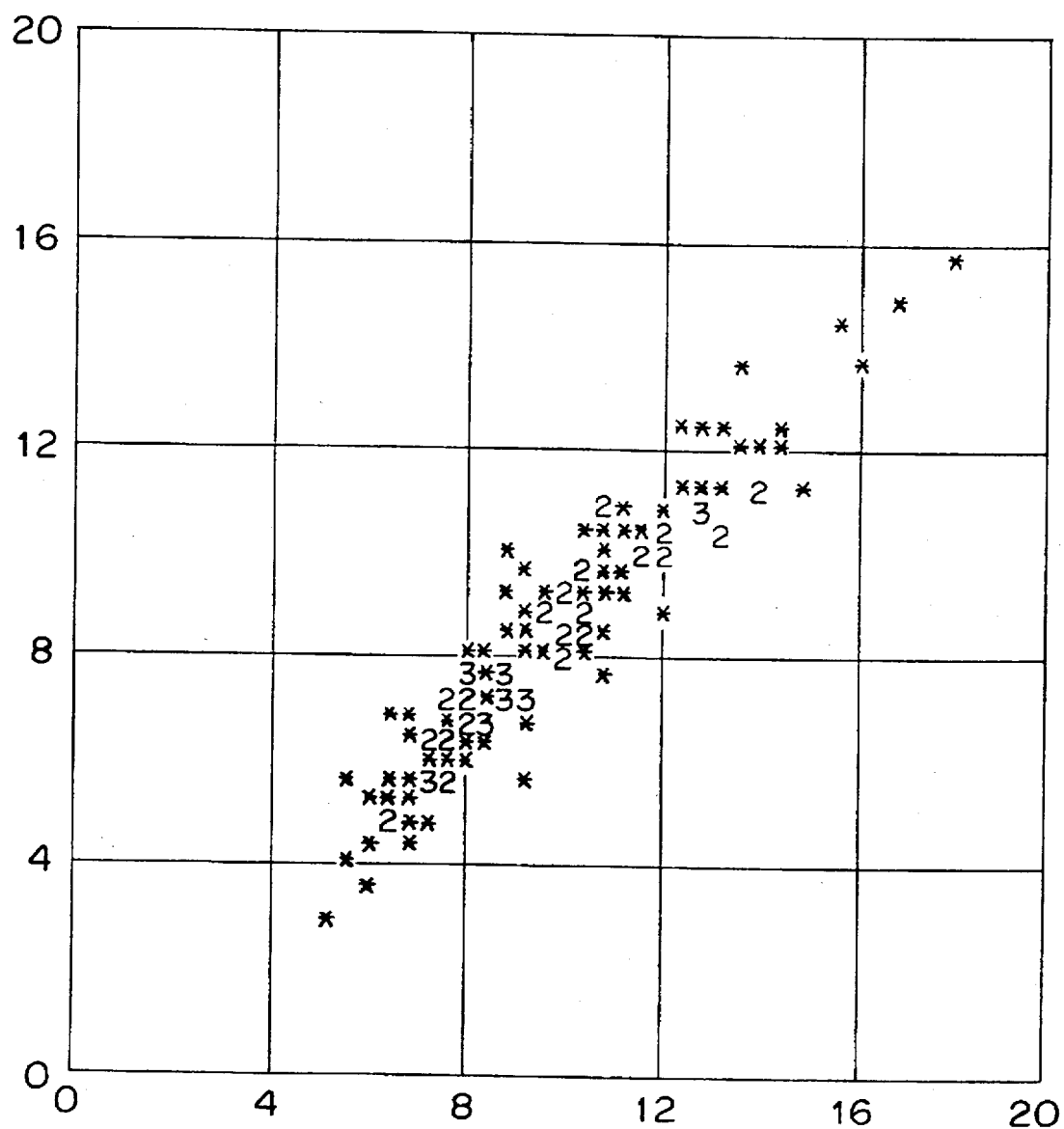
FIG. 4 shows a comparison of results obtained in Example 2 of the present invention as compared to a standard glycohemoglobin procedure (Helena Labs).

The results obtained as compared to a standard procedure are shown in FIG. 4.

(c) Readout With Custom Light Source and Reader

The same samples and capillaries as described earlier were also read in an engineering prototype, in which the light source and filter were replaced by light emitting diodes supplying light at 560 and 630 nm. The on-off timing was translated to voltage in a single measuring photodiode. Absorbance at 560 nm and 630 nm was determined. In this prototype, the optical measuring capillary was manually positioned first with the resin and then with the free solution in the light path to obtain the measurement results.

Figure 5:
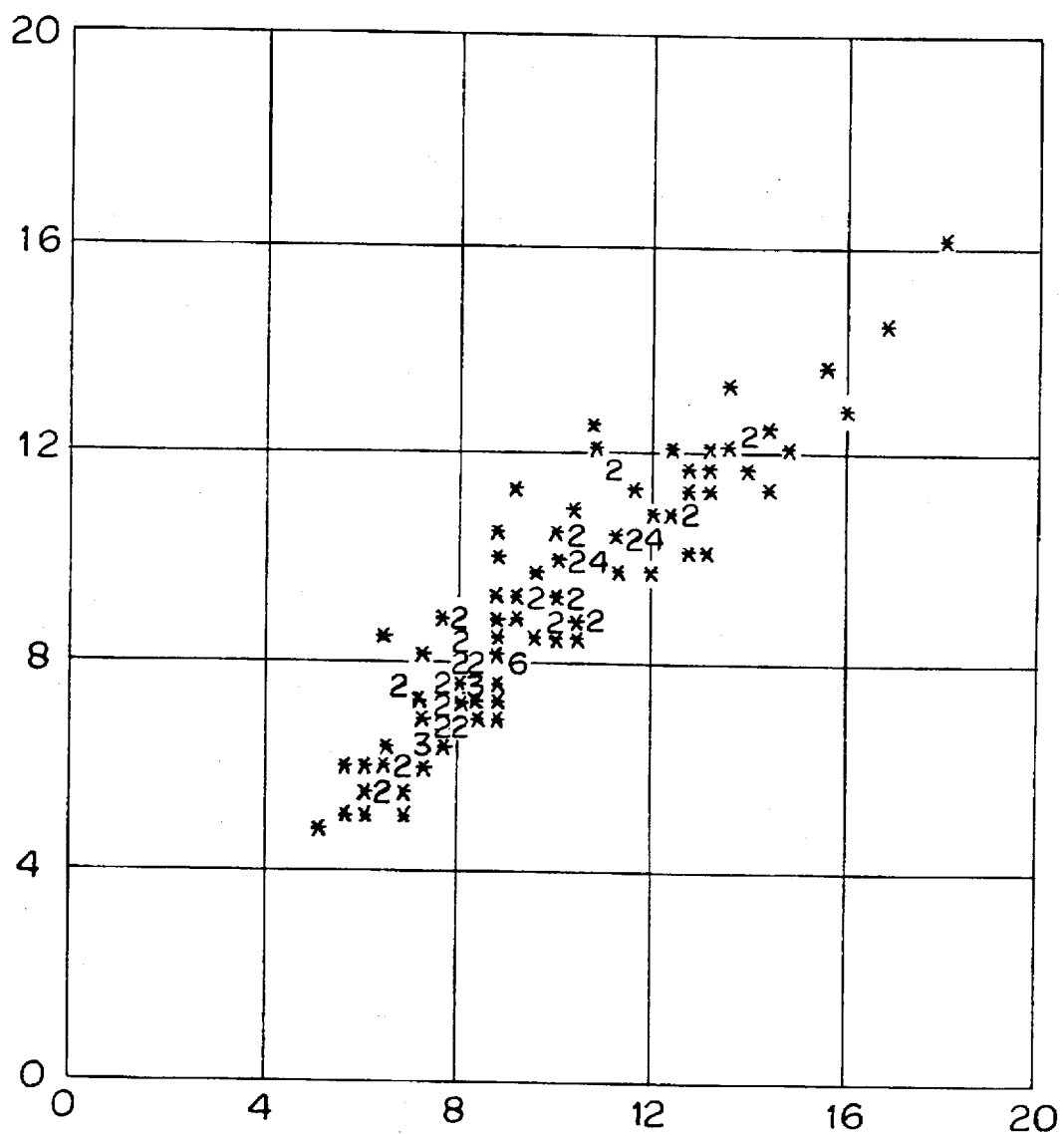
FIG. 5 shows the results obtained in Example 3 as compared to a standard procedure (Helena Labs) for measuring glycohemoglobin.

The results as compared to a standard procedure are shown in FIG. 5. The correlations of the measurements in FIGS. 3–5 with a standard procedure were very high:

| Device | Figure | Correlation |
| --- | --- | --- |
| Plate Reader | 3 | 0.93 |
| QBC Autoread | 4 | 0.95 |
| Custom Reader | 5 | 0.92 |

Comparison of the three measuring methods, with very different optical paths, shows them all to be equally useful.

EXAMPLE 2

Hemoglobin and Glycohemoglobin Measurement by Fluorescence Quenching

Inserting a fluorescent compound such as 8-hydroxy-1,3, 5-pyrene trisulfonate (HPT) into the allosteric pocket of the hemoglobin molecule causes quenching of the strong fluorescence of HPT. This quenching has also been described by MacQuarrie and Gibson in *J. Biol. Chem*, 274 (18): 5686–5694. HPT fluorescence quenching by hemoglobin is quantitative, and has been found to be independent of the glycation of hemoglobin. It was also surprisingly discovered that the fluorescence decrease due to competitive absorption of light by hemoglobin provides a sensing means which is independent of quenching due to ligand binding, provided that either excitation or fluorescence wavelengths, or both, of the fluorochrome overlap an absorption wavelength of hemoglobin.

In one embodiment of the present invention, quenching of HPT fluorescence is used as the means for measuring total hemoglobin. The further reduction of fluorescence, especially in the region of the particles, is due to reduced transmission of the exciting and emitted light through the hemoglobin adsorbed to the particulate. In one embodiment of the invention, this reduced transmission is measured by the reduced fluorescence and is then recalculated as an optical absorbance (optical density) resulting from the presence of hemoglobin.

Purified hemoglobin with varying proportions of glycohemoglobin was prepared. A standardized volume of each of three dilutions of the prepared hemoglobins was put into a reaction vessel using Reagent B. Reagent B was identical to Reagent A of Example 1 except for the addition of 111 mM 8 hydroxy-1,3,5-pyrene trisulfonate to the ammonium acetate/magnesium chloride buffer, pH 8.0

Samples were prepared for optical measurement as in Example 1.

Fluorescence excitation was accomplished with a white light source supplied with a blue filter transmitting only in the range of 460 to 490 nm. Fluorescent light was collected and measured after passage through a green filter that transmitted light between 530 and 650 nm and specifically rejected the excitation wavelengths.

For the purpose of simple calculations, the decrease in fluorescence observed in the sample compared tea blank with no hemoglobin is treated as absorbance.

$$OD\ solution = \log \frac{(FL\ solution\ blank)}{(FL\ solution\ sample)}$$

$$OD\ particulate = \log \frac{(FL\ sample\ solution \times B)}{(FL\ sample\ resin)}$$

B is an adjustment required for differences in collection of fluorescence light in the region of the resin as compared to the region of the solution. B is dependent on the numerical aperture of the light collecting lens in front of the sensor and differs for each instrument design as well as for each type of resin used.

As can be seen in the examples described below, OD solution yields a result which closely correlates to the total hemoglobin in the sample. Likewise, OD resin yields a result that correlates with glycohemoglobin in the resin, but this result is not independent of the total hemoglobin in the sample. Therefore, the computation of percent glycohemoglobin in the sample is:

$$GHb\ \% = 100 \times \frac{S\ (OD\ resin - C \times OD\ solution \times OD\ resin)}{OD\ solution}$$

where S is a slope adjustment of a regression equation and C is an adjustment related to the free volume as explained in Embodiment 1.

Figure 6:
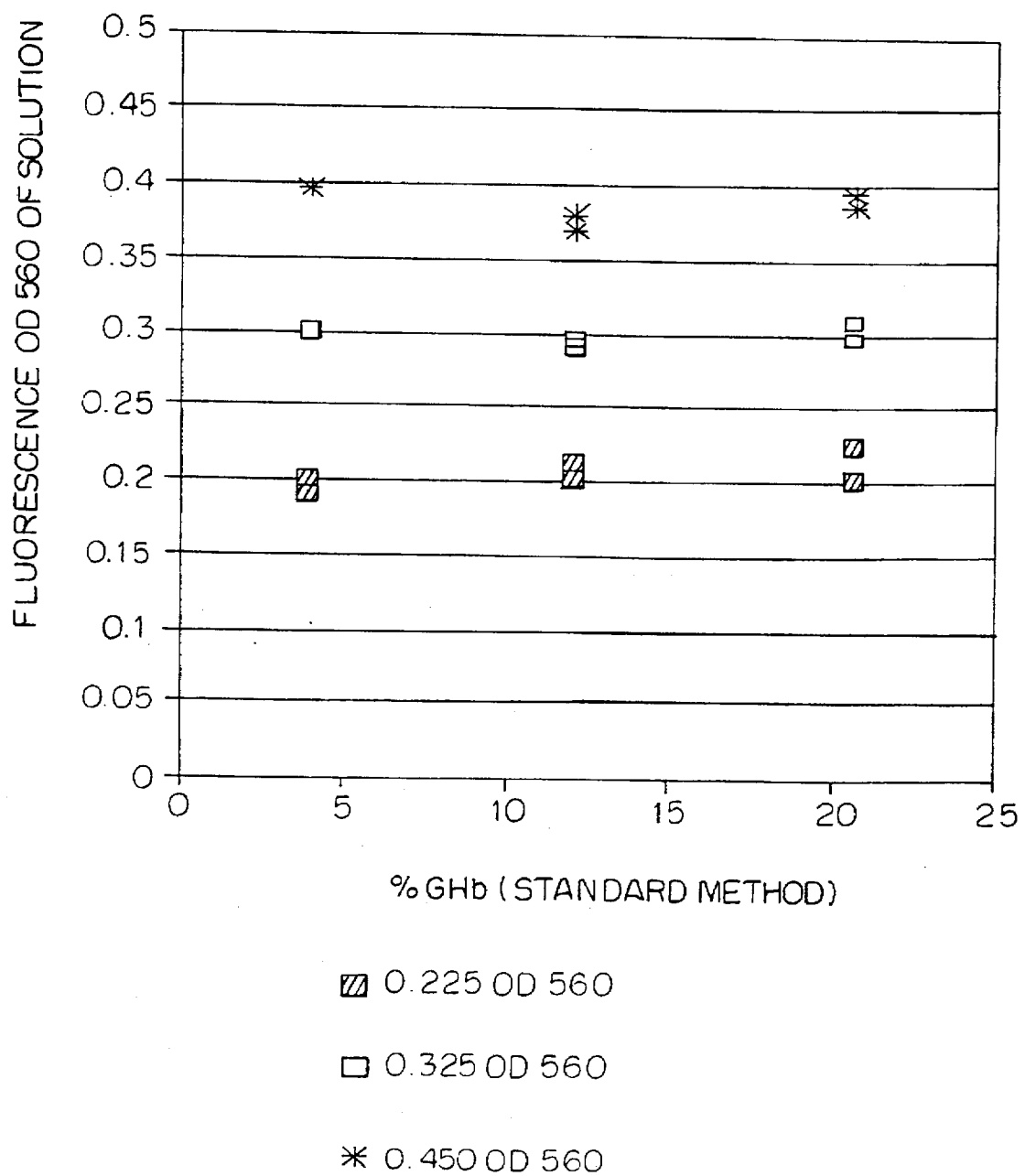
FIG. 6 shows the correlation between hemoglobin with a standard spectrophotometric measurement and the fluorescence measurement as obtained in Example 4.

The results for the hemoglobin determination are expressed as OD solution, and are given in FIG. 6, compared to OD units measured on an independent spectrophotometer at 410 nm on the diluted samples. Absolute measure of hemoglobin requires an absolute standard, which was not tested. Therefore, the relationship is provided solely as a comparison of the absorbencies. These can, however, be easily standardized by one skilled in this art.

It can be seen from FIG. 6 that the correlation between hemoglobin with a standard spectrophotometric measurement and the fluorescence measurement is very high. The regression equation may therefore be used to provide results at intermediate values.

Similar experiments were performed in a reagent excluding the resin. The resin is not required when only total hemoglobin is to be determined. The results provided equally good correlation.

Similar determinations were made for glycohemoglobin. The results are given in FIG. 7. The measurement results are expressed as proportions, which may be translated to glycohemoglobin percent. Comparison measurements were made with a standard commercially available glycohemoglobin kit, Pierce Glycogel II.

It can be seen that the results correlate very well over the whole range of expected clinical values. Therefore, the regression equation may be used to extrapolate results from measurements of unknown samples.

Calculations of results for glycohemoglobin may also be derived directly from the voltage measurement of the fluorescence sensor made in the region of the solution and the region of the particles. A simple ratio is derived as follows:

$$Ratio = \frac{Volts\ (fluorescence)\ particulates}{Volts\ (fluorescence)\ solution}$$

Figure 7:
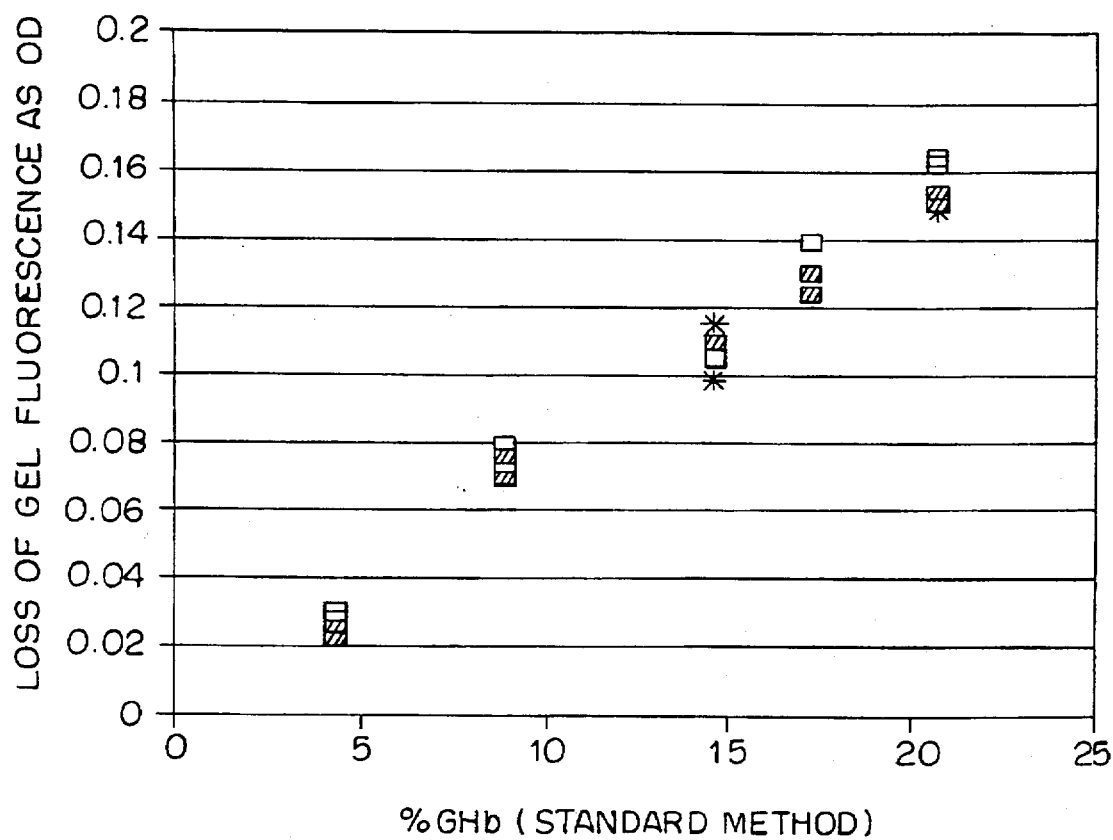
FIG. 7 shows measurement results of Example 5 as compared with a standard commercially available glycohemoglobin kit (Pierce).
Figure 8:
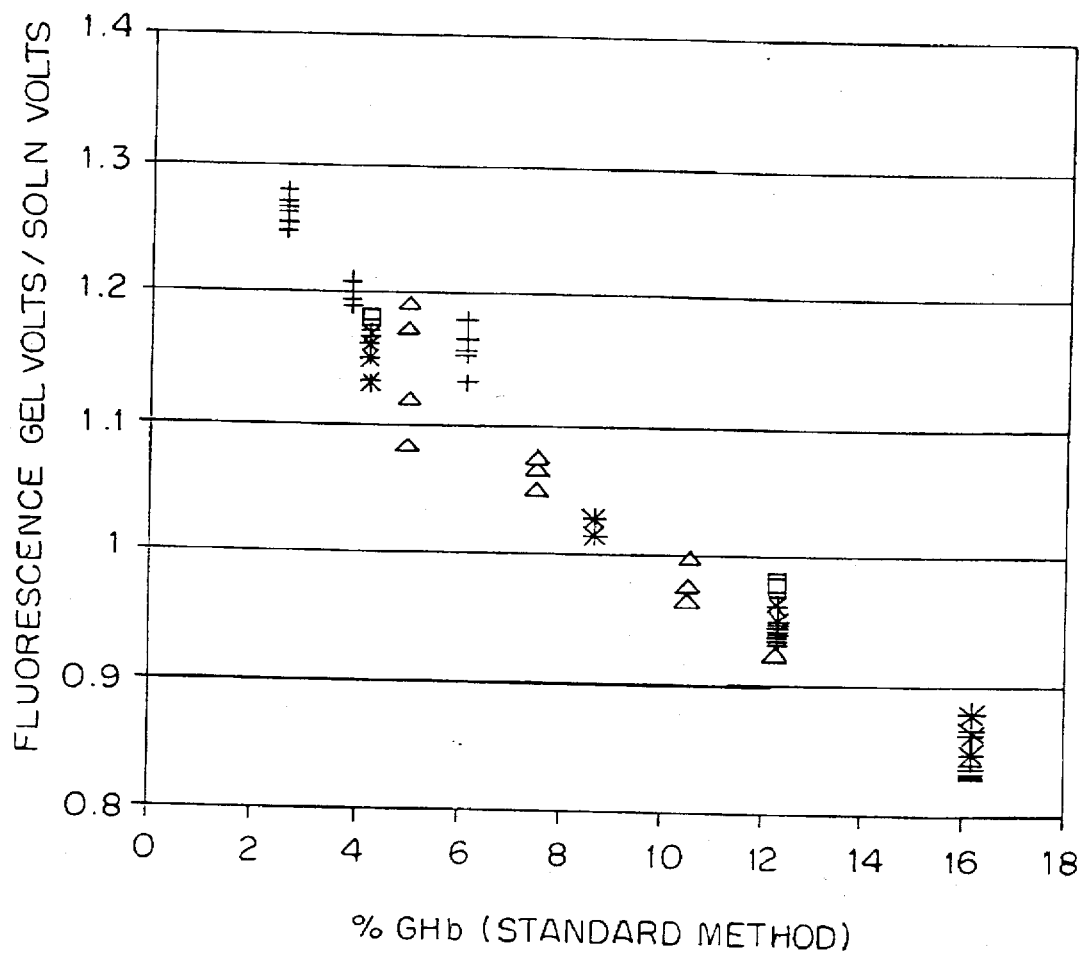
FIG. 8 shows the results obtained in Example 6 using the same comparison as in FIG. 7.

The results are shown in FIG. 8, using the same comparison as in FIG. 7. It can be seen that this simple ratio provides excellent correlation with a reference method over the whole range of clinical values. Therefore, the regression equation may be used to extrapolate results from measurements of unknown samples.

EXAMPLE 3

Glycohemoglobin Measurement by Refractive Light Loss and Hemoglobin by Fluorescence.

The refraction of light by the particles is influenced by the solid mass contained in the particles. The solid mass increases as more constituent is adsorbed onto the particles. This refractive light loss provides a means for directly measuring the mass of constituent independent of a specific absorbing wavelength.

In this example, in addition to measuring fluorescence of the solution as in Example 2, optical light loss was measured through the capillary at 630 nm, using a red LED at about 630 nm as the source. The readings were compared with a blank and absorbencies (OD) were computed.

By subtracting the OD solution from the OD resin, an estimate of glycohemoglobin attached to the resin was made. This estimate was based on the increase of refractive index of the resin due to its increased mass when glycohemoglobin was attached to the resin.

The total hemoglobin obtained by fluorescence measurement was used to normalize absorbance at 630 nm.

Figure 9:
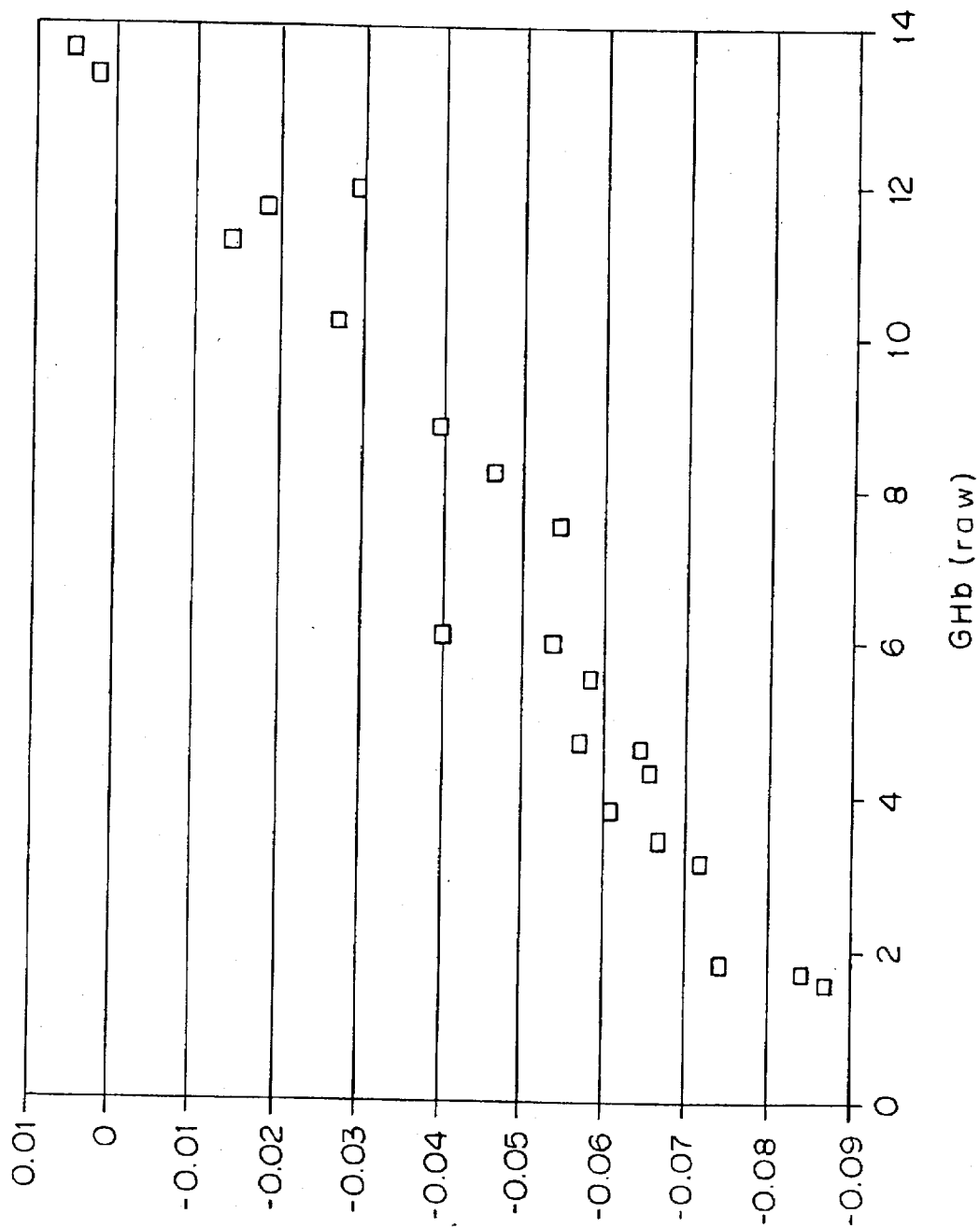
FIG. 9 shows the results obtained in Example 7 as compared with the Pierce Glycogel method.

The results are given in FIG. 9 with the same comparison method to Pierce Glycogel II. It can be seen that the correlation between the reference method and the experimental method is excellent, and therefore, the regression equation may be used to compute glycohemoglobin of samples where the glycohemoglobin is not known.

EXAMPLE 4

Noncovalent Attachment of Affinity Reagent to Particles

A dimer of aminophenyl boronic acid was synthesized, in which a spacer arm of at least six carbon atoms was between the two amino groups.

An acid reducing Schiff reagent was prepared from meta aminophenyl boronic acid by reacting the meta aminophenyl boronic acid overnight with 0.5N hydrochloric acid and 1% by weight of sodium metabisulfite. To the Schiff reagent was next added repeatedly small amounts of 0.1% glutaraldehyde in 0.1N HCl until, one hour after an addition, the test for aldehyde using a basic fuchsin Schiff reagent was positive. At this point, it was assumed that the m-aminophenyl boronic acid had been used up and a preponderance of dimer had been formed.

By adding an excess of disodium phosphate, the pH was brought to 8 and sodium borohydride was added, thus providing a stable imino compound with a preponderance of dimers.

Salts were removed from this dimer preparation and the desired dimer was concentrated by mixing with a dextran solid support, such as Sephadex G 25. The compounds containing boronic acid adhered to the dextran, while the salts could be eluted. The desired dimer may then be eluted in various solutions, such as an acidified methanol.

EXAMPLE 5

Competitive Assay with Particulate Analyte Analogue

This is a competitive binding assay for a glycated analyte. A lectin is used as an affinity molecule. An analog to the analyte is attached to the particles on a molecular arm long enough to make the analog accessible from solution. A lectin specific for the same analyte, such as concanavalin A for a mannose-bearing analyte (e.g., blood group substance A) is also provided. This lectin is optionally made fluorescent, for example with fluorescein isothiocyanate. When a sample containing an unknown amount of the analyte is mixed with the analogue-bearing particles and with the lectin, the fluorescing lectin distributes itself competitively between the solution and the particles. If, for example, there is no analyte in the sample, all of the fluorescing lectin will be adsorbed onto the particles. The proportions of particles and lectin are arranged so that the amount of analyte in a sample may be detected or measured.

If the lectin is not made fluorescent, it may still be measured by its effect on light scattering by particular to which it has complexed.

This test can be used for blood typing as well as for detecting contaminating blood types in a sample. Fetal red cells in maternal blood is an example of such contamination.

A partial list of pairs of lectin and blood type which can be used is as follows:

| 1. *Griffonia simplifolia* | I-A$_4$ | N-Acetyl galactosamine A |
| 2. *Griffonia simplifolia* | I-B$_4$ | Galactose B |
| 3. *Laburnum alpinum* | I | Oligo N-acetyl glucosamine O |

Another use of the present invention is for detection of circulating specific antibodies in plasma. In this case, the particles bear competitive antibody, while a fluorescing antigen is dissolved in the solution. The assay is a competitive assay, and the proportion of fluorescing antigen which remains in solution is inversely related to the amount of antibody in the plasma. This assay can be used to test for antibodies to hepatitis virus and AIDS virus.

Circulating antigen can be tested for by attaching antigen analogue to the particles and using fluorescently labeled antibody to the analyte as the marker.

EXAMPLE 6

Use of Pair of Particle-Blocked Wavelengths as Internal Control

In the methods described above, it was necessary to fractionate the treated sample into a particle-rich and particle-free zones, so as to control for the effects of unbound constituents. However, this fractionation is unnecessary if a second pair of wavelengths exist such that (a) the particles block light at both wavelengths, and (b) the analyte absorbs substantially more light at one wavelength than at the other. If the particles do not inherently have this property (a) they may be conjugated to a blocking agent which has this effect. In this example, chlorophyll "a" is used as a blocking agent.

Both hemoglobin and chlorophyll are porphyrin compounds. Although they have in common one absorption peak at around 410 nm, the "Sorret band", their absorption bands are otherwise different and do not overlap.

Beads of boronic acid affinity agarose were saturated with chlorophyll "a". The saturated beads have optical characteristics similar to chlorophyll "a" in solution in that they absorb at 400–450 nm, they are opaque from 650 to 680 nm, and they transmit light well between 450 and 650 nm. These beads retain their specific chemical affinity character.

Applying appropriate correction factors applied to adjust for incomplete transmission at 450–650 nm and for light scatter effects, it is possible to calculate % glycohemoglobin making four wavelength measurements on individual microtiter plate wells containing buffer at pH 8.0, lysing agent, a small portion of whole blood, and affinity beads containing chlorophyll a which partially obscure the light path.

The following table shows the effect of incident light at four different wavelengths.

| Wavelength | Hemoglobin | Particles Bearing Chlorophyll "a" |
|---|---|---|
| 670 nm | transmits | adsorbs |
| 410 | absorbs | absorbs |
| 630 | transmits | transmits |
| 560 | absorbs | transmits |

Light of wavelengths 670 and 410 will be received by the sensor only if they do not hit a particle, and, in the case of 410, it will be reduced in intensity as a result of absorbance by hemoglobin in the light path. Light of wavelengths 630 and 560 will be indifferent to the particles, but 560 will be attenuated by hemoglobin.

With appropriate constants and corrections for degrees of transparency in various wavelength readings, all of which may be determined experimentally, the percent glycohemoglobin in the sample is:

$$GHB\% = \frac{(Abs\ 560 - Abs\ 630) - (Abs\ 410 - Abs\ 670)}{(Abs\ 560 - Abs\ 630)}$$

In this embodiment, fractionation is unnecessary, as light which has not passed through the particles can be identified on the basis of its transmission at 630 nm and 560 nm.

Moreover, in this embodiment, there is no need for a blank, the extra wavelengths serving the same purpose.

With this method, it is possible to perform specific hemoglobin analysis, such as glycohemoglobin, in a single well of a microtiter plate reader. This is yet a further improvement in efficiency over the capillary tube method.

EXAMPLE 7

Size-Exclusion Assay

Another embodiment is particularly suited to assaying large molecules. The affinity reagent is a small molecule which intrinsically, or as a result of labeling (e.g., with a fluorophore or chromophore) is optically detectable. The affinity reagent is not bound to the particles, but the pore size of the particles is such that the small molecule, but not the complex of the analyte and the affinity reagent, can diffuse into the particles.

In the absence of analyte, the affinity reagent will be in equal concentration in both the particles and in solution. If analyte is present, it will capture the affinity reagent, reducing the concentration of the latter in the pores of the particles. This will alter the relative optical readings of the particle-rich and particle-free zones.

This form of the assay may be used to advantage when the intrinsic optical properties of the large molecular weight analyte do not offer sufficient optical contrast to analyte-free sample, or when it is more convenient to prepare the labeled small molecule than to attach the particle to the affinity reagent or to label an analyte analogue. Since the particle is not conjugated to another reagent, the same particles may be used for many different assays. A larger range of particles is also made available. For example, more transparent acrylic resin particles may be used, even without attaching the affinity ligand.

This method can be used to measure soluble starch. The large molecule is starch, and the small molecule may be a dansyl derivative of m-aminophenyl boronic acid, sold under the name of Fluorobora I by Polysciences, Inc. uses particles of crosslinked 6% agarose, such as Sepharose 6CL, from Pharmacia, Inc., which excludes molecules whose molecular weight is greater than $4 \times 10^6$, such as starch.

Another example would be an assay for a chromosome or large chromosomal fragment including a particular DNA sequence. The affinity reagent would be a complementary DNA probe which had been fluorescently labeled. This would hybridize to the target DNA, if present.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

We claim:

1. A method for measuring one or more analytes in a sample comprising adding substantially transparent particles to a sample solution;

incubating the particles and an affinity reagent with the sample to form a mixture;

fractionating the mixture to form a particle-rich fraction and a substantially particle-free fraction in fluid contact within a single container, the analyte being partitioned, as a result of binding to said affinity reagent, to concentrate it in one of said fractions;

optically reading the particle-rich fraction in said container at an analyte-detecting wavelength and a control wavelength;

optically reading the substantially particle-free fraction in said container at said analyte-detecting and said control wavelength;

said particle rich and particle free fractions being still in fluid contact in said container at the time of said readings;

correlating the readings through the particle-rich fraction and the substantially particle-free fraction of the sample with similar readings through a "blank" containing similar particles in a buffer solution, to obtain a quantitative determination of at least one analyte originally present in the sample, said correlating correcting the determination for the optical properties of the particle after absorption of analyte and the optical properties of unbound constituents of the sample which are present in the free volume of the particle-free fraction.

2. The method according to claim 1 wherein the particles are attached to the affinity reagent.

3. The method according to claim 2 wherein the affinity reagent is selected from the group consisting of carbohydrates, lectins, antibodies, antigens, enzymes, enzyme substrates, and enzyme inhibitors.

4. The method according to claim 1 wherein said particles are selected from the group consisting of dextran, agarose, agar, deacetlytated chitin, and starch.

5. The method according to claim 1 wherein one analyte is glycosylated hemoglobin.

6. The method according to claim 5 wherein a second analyte is unglycosylated hemoglobin.

7. The method according to claim 5 wherein said mixture is fractionated by centrifugation.

8. The method according to claim 1 wherein said fractionation is effected by permitting the particles to settle under the influence of gravity.

9. The method according to claim 1 wherein said fractionation is effected by collecting said particles on a frit.

10. The method of claim 1 in which an analyte analogue is also incubated with the sample, and the analyte analogue competes with the analyte for binding to the affinity reagent.

11. The method of claim 10 in which the analyte analogue is optically detectable, either intrinsically or as a result of conjugation to an optically detectable label, and the affinity reagent is conjugated to the particles.

12. The method of claim 10 in which the affinity reagent is optically detectable, either intrinsically or as a result of conjugation to an optically detectable label, and the analyte analogue is conjugated to the particles.

13. The method of claim 1 in which the particles are porous particles having pores of predetermined pore size, the affinity reagent is soluble and optically detectable, either intrinsically or by virtue of a label, the affinity reagent binds to the analyte to form a complex, and the pore size of the particles is chosen so that the affinity reagent can enter the pores but the complex of the affinity reagent and the analyte is substantially excluded from the pores of the particles.

14. The method of claim 6 in which the analyte competes with an analyte analogue which is optically detectable, either intrinsically or as a result of conjugation to an optically detectable label, for binding to the affinity reagent.

15. The method of claim 1 wherein the affinity reagent has a boronyl group through which it binds to glycated analytes.

16. The method of claim 1 wherein the particles are carbohydrate particles.

17. The method of claim 1 wherein the particles are plastic particles.

18. The method of claim 17 wherein the particles are polystyrene particles.

* * * * *

UNITED STATES PATENT AND TRADEMARK OFFICE
CERTIFICATE OF CORRECTION

PATENT NO. : 5,674,699
DATED : October 7, 1997
INVENTOR(S) : Alexander Saunders; Michael Allan Zarowitz It is certified that error appears in the above-identified patent and that said Letters Patent is hereby corrected as shown below:

Column 10,
after line 61, insert:
--In the figure:
$F(X) = .87 (69* X)$
Coefficient of determination R - squared = .87
Coefficient of correlation =.93
Standard error of estimate = .72
Number of points plotted = 130.--

Column 10,
after line 64, insert:
--In the figure:
$F(X) = .48 (.91* X)$
Coefficient of determination R - squared = .9
Coefficient of correlation = .95
Standard error of estimate = .77
Number of points plotted = 130.--

Column 10,
after line 68, insert:
--In the figure:
$F(X) = 1.38 (.78* X)$
Coefficient of determination R - squared = .85
Coefficient of correlation = .92
Standard error of estimate = .85
Number of points plotted = 130.--

Column 11,
after line 3, insert:
--In the figure:
FLOD 560 Soln v OD 560:
$y = 0.807X + 0.028$
$r = 0.995$.--

UNITED STATES PATENT AND TRADEMARK OFFICE
CERTIFICATE OF CORRECTION

PATENT NO. : 5,674,699
DATED : October 7, 1997
INVENTOR(S) : Alexander Saunders; Michael Allan Zarowitz It is certified that error appears in the above-identified patent and that said Letters Patent is hereby corrected as shown below:

Column 11,
after line 6, insert:
--In the figure:
Linear regression:
y = 0.008X - 0.004
r = 0.994.--

Column 11,
after line 8, insert:
--In the figure:
y = -0.028X + 1.302
r = -0.991
n=83.--

Column 11,
after line 10, insert:
--In the figure, r = 0.983.--

Signed and Sealed this

Fourteenth Day of August, 2001

*Attest:*

NICHOLAS P. GODICI
*Attesting Officer*          *Acting Director of the United States Patent and Trademark Office*